(12) United States Patent
Briand et al.

(10) Patent No.: US 9,243,030 B2
(45) Date of Patent: Jan. 26, 2016

(54) OPTICALLY PURE COMPOUNDS FOR IMPROVED THERAPEUTIC EFFICIENCY

(75) Inventors: Jean Paul Briand, Strasbourg (FR); Gilles Guichard, Gradignan (FR); Jose Courty, Villecresnes (FR); Robert H. Zimmer, Mulhouse (FR); Chantal Devin, Strasbourg (FR); Annie Lang, Wahlenheim (FR); Haixang Zhang, Illkirch Grafenstaden (FR); Ara Hovanessian, El Metn (LB)

(73) Assignees: Centre National De La Recherche Scientifique (CNRS), Paris (FR); ELRO Pharma Sarl, Mulhouse (FR)

( * ) Notice: Subject to any disclaimer, the term of this patent is extended or adjusted under 35 U.S.C. 154(b) by 758 days.

(21) Appl. No.: 12/993,427

(22) PCT Filed: May 22, 2008

(86) PCT No.: PCT/IB2008/053469
§ 371 (c)(1),
(2), (4) Date: Apr. 18, 2011

(87) PCT Pub. No.: WO2009/141687
PCT Pub. Date: Nov. 26, 2009

(65) Prior Publication Data
US 2011/0201559 A1 Aug. 18, 2011

(51) Int. Cl.
| | | |
|---|---|---|
| A61K 38/10 | (2006.01) | |
| C07K 7/02 | (2006.01) | |
| A61K 38/16 | (2006.01) | |
| C07K 5/068 | (2006.01) | |
| C07K 7/06 | (2006.01) | |
| A61K 38/00 | (2006.01) | |

(52) U.S. Cl.
CPC ............. *C07K 5/06086* (2013.01); *C07K 7/06* (2013.01); *A61K 38/00* (2013.01)

(58) Field of Classification Search
CPC ....... A61K 38/10; A61K 38/16; A61K 38/04; A61K 38/02; A61K 38/00; C07K 1/1072; C07K 1/1077; C07K 1/1075; C07K 1/06; C07K 1/00; C07K 2/00; C07K 5/02
USPC ........................................................ 514/18.6
See application file for complete search history.

(56) References Cited

U.S. PATENT DOCUMENTS

| | | |
|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,340,535 A | 7/1982 | Voisin et al. |
| 4,366,241 A | 12/1982 | Tom et al. |
| 4,472,509 A | 9/1984 | Gansow et al. |
| 5,021,236 A | 6/1991 | Gries et al. |
| 5,891,737 A | 4/1999 | Baindur et al. |
| 6,235,716 B1 | 5/2001 | Ben-Sasson |
| 6,783,952 B1 | 8/2004 | Brown et al. |
| 7,741,280 B2 | 6/2010 | Guichard et al. |
| 2004/0002457 A1 | 1/2004 | Hovanessian et al. |
| 2004/0047867 A1 | 3/2004 | Capron et al. |
| 2004/0186056 A1 | 9/2004 | Ruoslahti et al. |
| 2004/0248195 A1 | 12/2004 | Myllykallio et al. |
| 2005/0026860 A1 | 2/2005 | Lin et al. |
| 2008/0234464 A1 | 9/2008 | Ikeda et al. |
| 2011/0065649 A1* | 3/2011 | Courty et al. ................ 514/18.7 |

FOREIGN PATENT DOCUMENTS

| | | | |
|---|---|---|---|
| EP | 2033655 | 3/2009 | |
| WO | WO 95/29190 | 11/1995 | |
| WO | WO 00/61597 | 10/2000 | |
| WO | WO 03/102207 | 12/2003 | |
| WO | WO 2005/035579 | 4/2005 | |
| WO | WO 2007/125210 * | 8/2007 | ............. A61K 38/16 |
| WO | WO 2007/125210 * | 11/2007 | ............. A61K 38/00 |
| WO | WO 2007/125210 A2 | 11/2007 | |
| WO | WO 2009/141687 | 5/2008 | |
| WO | WO 2012/045750 | 10/2011 | |

OTHER PUBLICATIONS

Sakarellos-Daitsiotis et al. (Vaccine (2000) 18, 302-310.*
Nisole et al., The Journal of Biological Chemistry (2002) vol. 277, No. 23, pp. 20877-20886.*
Sakarellos-Daitsiotis et al., Vaccine (2000) 18, 302-310.*
Nisole et al., The Journal of Biological Chemistry (2002) 277(23), 20877-20886.*
Cushman et al., J.O.C. (1991) 56:416-67.*
Merrifield, R. B., Solid Phase Peptide Synthesis. I. The Synthesis of a Tetrapeptide, J. Am. Chem. Soc., 85(14), p. 2149-2154, 1963.

(Continued)

*Primary Examiner* — Karlheinz R Skowronek
*Assistant Examiner* — Catherine Mader
(74) *Attorney, Agent, or Firm* — Bryan D. Zerhusen; Locke Lord LLP

(57) ABSTRACT

The present invention relates to new optically pure compounds displaying an improved anticancer activity compared to previously known complex mixtures of stereoisomers thereof. Such compounds are of formula (I): wherein each X independently represents any amino acid; n is 0 or 1; m is an integer between 0 and 3; k is an integer of at least 3; Psi is a reduced bond of formula replacing the peptide amide bond between Lys and Pro; and wherein Lys residues in pseudopeptide units of said compound of formula (I) are either all in L configuration or all in D configuration. A method for preparing such compounds, and therapeutic uses thereof are also provided. The synthetic method involves the selective reduction of the peptide bond between Lys and Pro in a dipeptide intermediate with borane. The therapeutic uses are against cancer, inflammation and for wound healing.

22 Claims, 2 Drawing Sheets

(56) References Cited

OTHER PUBLICATIONS

Axen et al., Chemical Coupling of Peptides and Proteins to Polysaccharides by Means of Cyanogen Halides, Nature, vol. 214, pp. 1302-1304, 1967.
Goldenberg, D. M. et al., Use of Radiolabeled Antibodies to Carcinoembryonic Antigen for the Detection and Localization of Diverse Cancers by External Photoscanning, The New England Journal of Medicine, vol. 298, p. 1384-1388, 1978.
Goldenberg, D. M. et al., Experimental Radioimmunotherapy of a Zenografted Human Colonic Tumor (GW-39) Producing Carcinoembryonic Antigen, Cancer Research, vol. 41, p. 4353-4360, 1981.
Herlyn, M. et al., Monoclonal Antibody Detection of a Circulating Tumor-Associated Antigen. I. Presence of Antigen in Sera of Patients with Colorectal, Gastric, and Pancreatic Carcinoma, Journal of Clinical Immuology, vol. 2, pp. 135-140, 1982.
Pimm, M. V. et al., Tumour Localization of Monoclonal Antibody Against a Rat Mammary Carcinoma and Suppression of Tumour Growth with Adrianmycin-Antibody Conjugates, Cancer Immunol. Immunother., vol. 12, pp. 125-134, 1982.
Ettinger, D. S. et al., Phase I-II Study of Isotopic Immunogiobulin Therapy for Primary Liver Cancer, Cancer Treatment Reports, vol. 66, p. 289-297, 1982.
Herlyn, D. et al., IgG2a Monoclonal Antibodies Inhibit Human Tumor Growth Through Interactdion with Effector Cells, Proc. Natl. Acad. Sci., USA, vol. 79, pp. 4761-4765, 1982.
Hedin, A. et al., A Monoclonal Antibody-Enzyme Immunoassay for Serum Carcinoembryonic Antigen with Increased Specificity for Carcinomas, Proc. Natl. Acad. Sci., USA, vol. 80, pp. 3470-3474, 1983.
Bast, R. C. et al., A Radioimmunoassay Using a Monoclonal Antibody to Monitor the Course of Epithelial Ovarian Cancer, The New England Journal of Medicine, vol. 309, pp. 883-887, 1983.
Goldenberg, D. M. et al., Radioimmunodetection of Prostatic Cancer, J. A. M. A., vol. 250, pp. 630-635, 1983.
Goldenberg, D. M. et al., Carcinoembryonic Antigen Radioimmunodetection in the Evaluatioin of Colorectal Cancer and in the Detection of Occult Neoplasms, Gastroenterology, vol. 84, pp. 524-532, 1983.
Uhr, J. W. et al., The Use of Immunotoxins for the Treatment of Cancer, Monoclonal Antibodies and Cancer, Academic Press, Inc., pp. 85-98, 1983.
Vitetta, E. S. et al., Immunotoxins: A New Approach to Cancer Therapy, Science, vol. 219, pp. 644-650, 1983.
Schulz, G. et al., Monoclonal Antibody-Directed Effector Cells Selectively Lyse Human Melanoma Cells in vitro and in vivo, Proc. Natl. Acad. Sci., USA, vol. 80, pp. 5407-5411, 1983.
Capone, P. M. et al., Experimental Tumoricidal Effects of Monoclonal Antibody Against Solid Breast Tumors, Proc. Natl. Acad. Sci, USA, vol. 80, pp. 7328-7332, 1983.
Stewart, J. M. et al., Solid Phase Peptide Synthesis, Second Edition, Rockford, Pierce Chemical Company, 91, 1984.
Klug, T. L. et al., Monoclonal Antibody Immunoradiometric Assay for an Antigenic Determinant (CA 125) Associated with Human Epithelial Ovarian Carcinomas, Cancer Research, vol. 44, pp. 1048-1053, 1984, Mar. 1984.
Metzgar, R. S. et al., Detection of a Pancreatic Cancer-Associated Antigen (DU-PAN-2 Antigen) in Serum and Ascites of Patients with Adenocarcinoma, Proc. Natl. Acad. Sci., USA, vol. 81, pp. 5242-5246, 1984.
Papsidero, L. D. et al., Expression of Ductal Carcinoma Antigen in Breast Cancer Sera as Defined Using Monoclonal Antibody F36/22, Cancer. Research, vol. 44, pp. 4653-4657, 1984.
Pekary, A. E. et al., A New Monoclonal-Antibody Two-Site Solid-Phase Immunoradiometric Assay for Human Thyrotropin Evaluated, Clin. Chem., vol. 30/7, pp. 1213-1215, 1984.
Bellet, D. H. et al., Serum α-Fetoprotein Levels in Human Disease: Perspective From a Highly Specific Monoclonal Radioimmunoassay, Proc. Natl. Acad. Sci., USA, vol. 81, pp. 3869-3873, 1984.
Embleton, M. J. et al., Antigenicity and Drug Susceptibility of Human Osteogenic Sarcoma Cells "Escaping" A Cytotoxic Methotrexate-Albumin-Monoclonal Antibody Conjugate, Br. J. Cancer, vol. 49, pp. 559-565, 1984.
Vitetta, E. S. et al., Immunotoxins: A New Approach to Cancer Therapy, Biotechnology and Biol. Frontiers, Ed. P. H. Abelson, p. 73-85, 1984.
Carrasquillo, J. A. et al., Diagnosis of and Therapy for Solid Tumors with Radiolabeled Antibodies and Immune Fragments, Cancer Treatment Reports, vol. 68, pp. 317-328, 1984.
Zalcberg, J. R. et al., Tumor Immunotherapy in the Mouse with the Use of $^{131}$I-Labeled Monoclonal Antibodies, J. Natl. Cancer Inst., vol. 72, pp. 697-704, 1984.
Courtenay-Luck, N. et al., Antiboedy-Guided Irradiation of Malignant Lesions: Three Cases Illustrating a New Method of Treatment, The Lancet, vol. 1, p. 8 . 1441-1443, 1984.
Nepom, G. T. et al., Induction of Immunity to a Human Tumor Marker by in vivo Administration of Anti-Idiotypic Antibodies in Mice, Proc. Natl. Acad. Sci., USA, vol. 81, pp. 2864-2867, 1984.
Kaprowski, H. et al., Human Anti-Idiotype Antibodies in Cancer Patients: Is the Modulation of the Immune Response Beneficial for the Patient, Proc. Natl. Acad. Sci., USA, vol. 81, pp. 216-219, 1984.
Hayes, D. F. et al., Use of a Murine Monoclonal Antibody for Detectioin of Circulating Plasma DF3 Antigen Levels in Breast Cancer Patients, J. Clin. Invest., vol. 75, pp. 1671-1678, 1985.
Killian, C. S. et al., Prognostic Importance of Prostate-Specific Antigen for Monitoring Patients with Stage $B_2$ to $D_1$ Prostate Cancer, Cancer Research, vol. 45, pp. 886-891, 1985.
Epenetos, A. A. et al., $^{123}$I Radioiodinated Antibody Imaging of Occult Ovarian Cancder, Cancer, vol. 55, p. 984-987, 1985.
Chiou, R. et al., Localization of Human Renal Cell Carcinoma Xenografts with a Tumor-Preferential Monoclonal Antibody, Cancer Research, vol. 45, p. 6140-6146, 1985.
Jones, D. H. et al., Therapeutic Application of a Radiolabelled Monoclonal Antibody in Nude Mice Xenografted with Human Neuroblastoma: Tumoricidal Effects and Distribution Studies, Int. J. Cancer, vol. 35, pp. 715-720, 1985.
Lange, P. H. et al., Monoclonal Antibodies in Human Renal Cell Carcinoma and Their Use in Radioimmune Localization and Therapy of Tumor Xenografts, Surgery, vol. 98, pp. 143-150, 1985.
Liu, M.A. et al., Heteroantibody Duplexes Target Cells for Lysis by Cytotocis T Lymphocytes, Proc. Natl. Acad. Sci., USA, vol. 82, pp. 8648-8652, 1985.
Sears, H. F. et al., Phase II Clinical Trial of a Murine Monoclonal Antibody Cytotoxic for Gastrointestinal Adenocarcinoma, Cancer Ressearch, vol. 45, pp. 5910-5913, 1985.
Houghton, A. N. et al., Mouse Monoclonal IgG3 Antibody Detecting $G_{D3}$ Antibody Detecting $G_{D3}$ Ganglioside: A Phase I Trial in Patients with Malignant Melanoma, Proc. Natl. Acad. Sci., USA, vol. 82, pp. 1242-1246, 1985.
Remington's Pharmaceutical Sciences, 17$^{th}$ Edition, Title page and Prefaces, Mack Publishing Co., A. R. Gennaro edit, 1985.
Killian, C. S. at al., Relative Reliability of Five Serially Measured Markers for Prognosis of Progression in Prostate Cancer, J. Natl. Cancer Inst., vol. 76, pp. 179-185, 1986.
Siccardi, A. G. et al., Multicenter Study of Immunoscintigraphy with Radiolabeled Monoclonal Antibodies in Patients with Melanoma, Cancer Research, vol. 46, pp. 4817-4822, 1986.
Philben, V. J. et al., The Effect of Tumor CEA Content and Tumor Size on Tissue Uptake of Indium 111-Labeled Anti-CEA Monoclonal Antibody, Cancer, vol. 57, pp. 571-576, 1986.
Hwang, K. M. et al., Dynamic Interaction of $^{111}$Indium-Labeled Monoclonal Antibodies With Surface Antigens of Solid Tumors Visualized in Vivo by External Scintigraphy, J. Natl. Cancer Inst., vol. 76, p. 849-855, 1986.
Deguchi, T. et al., Effect of Methotrexate-Monoclonal Anti-Prostatic Acid Phosphatase Antibody Conjugate on Human Prostate Tumor, Cancer Research, vol. 46, pp. 3751-3755, 1986.
Kaltovich, F. A. et al., Radioimmunotherapy (RAIT) of Human Colonic Cancer Xenocrafts With Anti-Carcinoembryonic Antigen (CEA) Antibody, J. Nucl. Med., vol. 27, p. 897, 1986.

(56) References Cited

OTHER PUBLICATIONS

Perez, P. et al., Specific Targeting of Human Peripheral Blood T Cells by Heteroaggregates Containing Anti-T3 Crosslinked to Anti-Target Cell Antibodies, J. Exper. Med., vol. 163, pp. 166-178, 1986.
Feuerstein, N. et al., Identificaiotn of Numatrin, the Nuclear Matrix Protein Associated with Induction of Mitogenesis, as the Nucleolar Protein B23. Implication for the Role of the Nucleolus in Early Transduction of Mitogenic Signals, J. Biol. Chem., 263(22), p. 10608-10612, 1988.
Atherton, E. et al., Solid Phase Peptide Synthesis: A Practical Approach, Title page and Contents, Oxford, England, IRL Press, 1989.
M. Cushman, et al., Development of Methodology for the Synthesis of Stereochemically Pure Pheψ[CH2N]Pro Linkages in HIV Protease Inhibitors, J Org. Chem. 56, pp. 4161-4167, 1991.
Okawa et al., Journal of Immunological Methods, vol. 149, pp. 127, 1992.
Rot, A., Neutrophil Attractant/Activation Protein-1 (Intrleukin-8) Induces in vitro Neutrophil Migration by Haptotactic Mechanism, Eur. J. Immunol., vol. 23, pp. 303-306, 1993.
Gregoriadis (Editor), Liposome Technology, $2^{nd}$ Edition, vols. I-III, CRC Press, Boca Raton, Florida, Ann Arbor, Michigan, London, United Kingdom, Tokyo, Japan, 1993.
Carpino, L. A., 1-Hydroxy-7-azabenzotriazole. An efficient Peptide Coupling Additive, J. Am. Chem. Soc., 115(10), pp. 4397-4398, 1993.
Kreuter et al., Passage of Peptides Through the Blood-Brain Barrier with Colloidal Polymer Particles (Nanoparticles), Brain Research, vol. 674, pp. 171-174, 1995.
Pardridge et al., Vector-Mediated Delivery of a Polyamide (Peptide) Nucleic Acid Analogue Through the Blood-Brain Barrier in vivo, NPNAS USA, vol. 92, pp. 5592-5596, 1995.
Boado, Antisense Drug Delivery Through the Blood-Braiin Barrier, Advanced Drug Delivery Reviews, vol. 15, pp. 73-107, 1995.
Lasic et al., The "Stealth" Liposome: A Prototypical Biomaterial, Chemical Reviews, vol. 95, pp. 2601-2627, 1995.
Ishiwata et al., Physical-Chemistry Characteristics and Biodistribution of Poly(ethylene glycol)-Coated Liposomes Using Poly(oxyethylene) Cholesteryl Ether, Chem. Pharm. Bull, vol. 43, pp. 1005-1011, 1995.
Majno, G. et al., Apoptosis, Oncosis, and Decrosis. An Overview of Cell Death, American Journal Pathology, 146(1), pp. 3-15, 1995.
Engleton et al., Bioavailability and Transport of Peptides and Peptide Drugs into the Brain, Peptides, vol. 9, pp. 1431-1439, 1997, Egleton.
O'Reilly, M. S. et al., Endostatin: An Endogenous Inhibitor of Angiogenesis and Tumor Growth, Cell, 88(2), pp. 277-285, 1997.
Larrucea, S. et al., Cellular Adhesion Mediated by Factor J, A Complement Inhibitor. Evidence for Nucleolin Involvement, J. Biol. Chem., 273(48), pp. 31718-31725, 1998.
Boado et al., Drug Delivery of Antisense Molecules to the Brain for Treatment of Alzheimer's Disease and Cerebral AIDS, Journal of Pharmaceutical Sciences, vol. 87, pp. 1308-1315, 1998.
Aldrian-Herrada et al., A Peptide Nucleic Acid (PNA) is more Rapidly Internalized in Cultured Neurons When Coupled to a Retro-Inverso Delivery Peptide. The Antisense Activity Depresses the Target mRNA and Protein in Magnocellular Oxytocin Neurons, Nucleic Acids Res., vol. 26, pp. 4910-4916, 1998.
Jolliet-Riant, et al., Drug Transfer Across the Blood-Brain Barrier and Improvement of Brain Delivery, Fundam. Clin. Pharmacol., vol. 13, pp. 16-26, 1999.
Emerich, D. F. et al., Bicompatibility of Poly (D-Lactide-co-Glycolide) Microspheres Implanted Into the Brain, Cell Transplant, vol. 8, pp. 47-58, 1999.
Schroeder, et al., Diffusion Enhancement of Drugs by Loaded Nanoparticles in Vitro, Prog. Neuropsychopharmacol. Biol. Psychiatry, vol. 23, pp. 941-949, 1999.
Dumler, I. et al., Urokinase-Induced Mitogenesis is Mediated by Casein Kinase 2 and Nucleolin, Curr. Bio., 9(24), pp. 1468-1476, 1999.

Tyler et al., Specific Gene Blockade Shows that Peptide Nucleic Acids Readily Enter Neuronal Cells in vivo, FEBS Letters, vol. 421, pp. 280-284, 1999.
Tyler et al., Peptide Nucleic Acids Targeted to the Neurotensin Receptor and Administered I.P. Cross the BloodBraiin Barrier and Specifically Reduce Gene Expression, PNAS USA, vol. 96, pp. 7053-7058, 1999.
Dhanabal, M. et al., Endostatin Induces Endothelial Cell Apoptosis, J. Biol. Chem., 274(17), pp. 11721-11726, 1999.
Xu et al., Inhibition of DNA Replication and Induction of S Phase Cell Cycle Arrest by G-Rich Oligonucleotides, J. Biol. Chem., vol. 276, pp. 43221-43230, 2001.
Harms, G. et al., Identification of Nucleolin as a New L-Selectin Ligand, Biochem. J., 360(Pt 3), pp. 531-538, 2001.
Sengupta, T. K. et al., Identification of nucleolin as an AU-Rich Element Binding Protein Involved in bcl-2 mRNA Stabilization, J. Biol. Chem., 279(12), pp. 10855-10863, 2004.
Otake, Y. et al., Retinoid-Induced Apoptosis in HL-60 Cells is Associated with Nucleolin Down-Regulation and Destabilization of Bcl-2 mRNA, Mol. Pharmacol., 67(1), pp. 319-326, 2005.
Takagi, M. et al., Regulation of p53 Translation and Induction After DNA Damage by Ribosomal Protein L26 and Nucleolin, Cell, 123(1), pp. 49-63, 2005.
Chan, H. J. et al., Nucleophosmin/B23-Binding Peptide Inhibits Tumor Growth and Up-Regulates Transcriptional Activity of p53, Biochem. Biophys. Res. Commun., 333(2), pp. 396-403, 2005.
Alete et al., Febs J., vol. 273, pp. 4668-4681, 2006.
Tate, A. et al., Met-Independent Hepatocyte Growth Factor-mediated regulation of cell adhesion of human prostate cancer cells, BMC Cancer, vol. 6, p. 197, 2006.
Turck, N. et al., Effect of Laminin-1 on Intestinal Cell Differentiation Involves Inhibition of Nuclear Nucleolin, J. Cell. Physio., 2006(2), pp. 545-555, 2006.
Grinstein, E. et al., Cell Cycle-Controlled Interaction of Nucleolin with the Retinoblastoma Protein and Cancerous Cell Transformation, J. Biol. Chem., 281(31), pp. 22223-22235, 2006.
Blondet, B. et al., Exogeneous Pleiotrophin Applied to Lesioned Nerve Impairs Muscle Reinnervation, Neurochem. Res., 31(7), pp. 907-913, 2006.
Otake, Y. et al., Overexpression of Nucleolin in Chronic Lymphocytic Leukemia Cells Induces Stabilization of bcl2 mRNA, Blood, 109(7), pp. 3069-3075, 2007.
Ugrinova, I. et al., Inactivation of Nucleolin Leads to Nucleolar Disruption, Cell Cycle Arrest and Defects in Centrosome Duplication, BMC Molecular Biology, 8(1), pp. 1-16, 2007.
Shi, H. et al., Nucleolin is a Receptor that <ediates Antiangiogenic and Antitumor Activity of Endostatin, Blook, 110(8), pp. 1899-1906, 2007.
Di Segni, A. et al., Identification of Nucleolin as New ErbB Receptor Interacting Protein, PLoS One, 3(6), e2310, pp. 1-9, 2008.
Stepanova, V. et al., Nuclear Translocation of Urokinase-Type Plasminogen Activator, Blood, 112(1), pp. 100-110, 2008.
Reyes-Reyes, E. M. et al., Cell-Surface Nucleolin is a Signal Transducing P-Selectin Binding Protein for Human Colon Carcinoma Cells, Exp. Cell Res., 314(11-12), pp. 2212-2223, 2008.
Destouches, D. et al., Suppression of Tumor Growth and Angiogenesis by a Specific Antagonist of the Cell-Surface Expressed Nucleolin, PLoS One, 3(6), e2518, pp. 1-12, 2008.
Soundararajan, S. et al., The Nucleolin Targeting Aptamer AS1411 Destabilizes Bcl-2 Messenger RNA in Human Breast Cancer Cells, Cancer Res., 68(7), pp. 2358-2365, 2008.
Qi, W. et al., NSC348884, A Nucleophosmin Inhibitor Disrupts Oligomer Formation and Induces Apoptosis in Human Cancer Cells, Oncogene, 27(30), pp. 4210-4220, 2008.
Bates, P. J. et al., Discovery and Development of the G-Rich Oligonucleotide AS1411 as a Novel Treatment for Cancer, Experimental and Molecular Pathology, 86(3), pp. 151-164, 2009.
Drecoll, E. et al., Treatment of Peritoneal Carcinomatosis by Targeted Delivery of the Radio-Labeled Tumor Homing Peptide bi-DTPA-[F3]2 into the Nucleus of Tumor Cells, PloS One, 4(5), e5715, pp. 1-9, 2009.

(56) References Cited

OTHER PUBLICATIONS

Fogal, V. et al., Cell Surface Nucleolin Antagonist Causes Endothelial Cell Apoptosis and Normalization of Tumor Vasculature, Angiogenesis, 12(1), pp. 91-100, 2009.

Page, N. et al., The Spliceosomal Phosphopeptide P140 Controls the Lupus Disease by Interacting with the HSC70 Protein and via a Mechanism Mediated by Hammadelta T Cells, PLos One, 4(4), e5273, pp. 1-13, 2009.

Ling, Y. et al., Endostar Induces Apoptotic Effects in HUVECs Through Activation of Caspase-3 and Decrease of Bcl-2, Anticancer Res., 29(1), pp. 411-417, 2009.

Inder, K. L. et al., Nucleophosmin and Nucleolin regulate K-Ras Plasma Membrane Interactions and MAPK Signal Transduction, J. Biol. Chem., 284(41), pp. 28410-28933, 2009.

PCT International Search Report for WO 2007/125210 dated Jun. 30, 2008.

PCT International Search Report for WO 2009/141687 dated Sep. 2, 2009.

Abbondanzo et al., 1990. "Acute Infectious Mononucleosis", Single Case Reports, 93(5) 698-702.

Allred et al., 1990. "Immunocytochemical Analysis of Estrogen Receptors in Human Breast Carcinomas", Arch Surg, 125, 107-113.

Alter, P. et al., Usefulness of cytokines interleukin-6 and interleukin-2R concentrations in diagnosing active infective endocarditis involving native valves, Am. J. Cardiol., vol. 89, p. 1400-1404, 2002.

Bates, P. et al., Antiproliferative activity of G-rich oligonucleotides correlates with protein binding, J. Biol. Chem., vol. 274, No. 37, p. 26369-26377, 1999.

Bucklin, S. E., An interleukin-6-induced acute-phase response does not confer protection against lipopolysaccharide lethality, Infect. Immun., vol. 61, No. 8, p. 3184-3189, 1993.

Callebaut, C. et al., Identification of V3 loop-binding proteins as potential receptors implicated in the binding of HIV particles to CD4(+) cells, J. Biol. Chem., vol. 273, No. 34, p. 21988-21997, 1998.

Callebaut, 1996, Virology, 218 pgs. 181-192 "Inhibition of HIV Infection by Pseudopeptides Blocking Viral Envelope Glycoprotein Mediated Membrane Fusion and Cell Death".

Callebaut, C. et al., Pseudopeptide TASP inhibitors of HIV entry bind specifically to a 95-kDa cell surface protein, J. Biol. Chem., vol. 272, No. 11, p. 7159-7166, 1997.

Christian, S. et al., Nucleolin expressed at the cell surface is a marker of endothelial cells in angiogenic blood vessels, J. Cell Biol., vol. 163, No. 4, p. 871-878, 2003.

Destouches et al., A Simple Approach to Cancer Therapy Afforded by Multivalent Pseudopeptides that Target Cell-Surface Nucleoproteins, Cancer Res 2011;71:3296-3305.

El Khoury et al., Targeting Surface Nucleolin with a Multivalent Pseudopeptide Delays Development of Spontaneous Melanoma in RET Transgenic Mice, *BMC Cancer* 2010, 10:325, pp. 1-12.

Elass, E. et al., Lactoferrin inhibits the lipposaccharaide-induced expression and proteoglycan-binding ability of IL-8 in human entothelial cells, Infect. Immun., vol. 70, No. 4, p. 1860-1866, 2002.

Fazekas, 2001, Microvascular Research, 62 pgs. 440-444 "Effect of HGF-like Basic Hexapeptides on Angiogenesis."

Fournel, S. et al., C3-symmetric peptide scaffolds are functional mimetics of trimeric CD4OL, Nat. Chem. Biol., vol. 1, No. 7, p. 377-382, 2005.

Ginsty, H. et al., Structure and functions of nucleolin, J. Cell Science, vol. 112, p. 761-772, 1999.

Hovanessian et al., The cell-surface-expressed nucleolin is associated with the actin cytoskeleton, Exp. Cell Res., vol. 261, p. 312-328, 2000.

Hovanessian, et al., Surface Expressed Nucleolin is Constantly Induced in Tumor Cells to Mediate Calcium-Dependent Ligand Internalization, PLoS ONE Dec. 2010, 5(12) : pp. 1-13.

Hruby et al., Conformational and Topographical Considerations in Designing Agonist Peptidomimetics from Peptide Leads, *Current Medicinal Chemistry*, 2000, 7, pp. 945-970.

Huang, Y. et al., The angiogenesis function of nucleolin is mediated by vascular endothelial growth factor and nonmuscle myosin, Blood, vol. 107, No. 9, p. 3564-3571, 2006.

Hurwitz, H. I., New agents in colon cancer, Clin. Adv. Hematol. Oncol., vol. 1, No. 7, p. 404405, 2003.

Kabbinavar, F. et al., Phase II, randomized trial comparing bevacizumab plus fluorouracil (FU)/leucovorin (LV) with FU/LV alone in patients with metastatic colorectal cancer, J. Clin. Oncol., vol. 21, No. 1, p. 60-65, 2003.

Kannan, K. et al., Animal models of rheumatoid arthritis and their revalence to human disease, Pathophysiology, vol. 12, p. 167-181, 2005.

Karima, R. et al., The molecular pathogenesis of endotoxic shock and organ failure, Mol. Med. Today, p. 123-132, 1999.

Kevil, C. G. et al., Essential role of ICAM-1 in mediating monocyte adhesion to aortic endothelial cells, Am. J. Physiol. Cell Physiol., vol. 281, p. 1442-1447, 2001.

Krust et al., Suppression of Tumorigenicity of Rhabdoid Tumor Derived G401 Cells by the Multivalent HB-19 Pseudopeptide that Targetrs Surface Nucleolin, Biochimie. Mar. 2011;93(3):426-433.

Krust et al., Targeting Surface Nucleolin with Multivalent HB-19 and Related Nucant Pseudopeptides Results in Distinct Inhibitory Mechanisms Depending on the Malignant Tumor Cell Type, BMC Cancer 2011, 11:333, pp. 1-22.

Krust et al., The anti-HIV pentameric pseudopeptide HB-19 is preferentially taken up in vivo by lympohoid organs where it forms a comples with nucleolin, PNAS, vol. 98, No. 24, p. 1409014095, Nov. 20, 2001.

Legrand, D. et al., Surface nucleolin participates in both the binding and endocytosis of lactoferrin in target cells, Eur. J. Biochem., vol. 271, p. 303-317, 2004.

Nakamura et al., 1987. "Variable Number of Tandem Repeat Markers for Human Gene Mapping"Science, 235, 1616-1622.

Nisole S. et al., The HB-19 pseudopeptide 5[Kpsi(CH2N)PR]-TASP inhibits attachment of T lymphocyte- and macrophage-tropic HIV to permissive cells, AIDS Res. Hum. Retroviruses, 16(3): 237-49, Feb. 10, 2000.

Nisole, S. et al., Anchorage of HIV on permissive cells leads to coaggregation of viral particles with surface nucleolin at membrane raft microdomains, Exp. Cell Res., vol. 276, p. 155-173, 2002.

Nisole, S. et al., The anti-HIV Pseudopeptide HB-19 forms a complex with the cell-surface-expressed nucleolin independent of heparin sulfate proteoglycans, J. Biol. Chem., vol. 274, No. 39, p. 27875-27884, 1999.

Order, S. E. et al., Int. J. Radiother. Oncol. Bio. Phys., vol. 8, p. 121, 1982. "New Immunotherapeutic and Diagnostic Approaches to Ovarian Cancer".

PCT International Search Report for PCT/EP2011/067337.

Peifer, et al, New Approaches to the Treatment of Inflammatory Disorders Small Molecule Inhibitors of p38 MAP Kinase, Current Topices in Medicinal Chemistry, 6, 113-149, 2006.

Phase I Trial in Patients with Malignant Melanoma, Proc. Natl. Acad. Sci., USA, vol. 82, pp. 1242-1246, 1985.

Prog. Neuropsychopharmacol. Biol. Psychiatry, vol. 23, p. 941-949, 1999.

Said, A. E. et al., Pleiotrophin inhibits HIV infection by binding the cell surface-expressed nucleolin, Febs J., vol. 272, p. 4646-4659, 2005.

Said, A. E. et al., The anti-HIV cytokine midkine binds the cell surface-expressed nucleolin as a low affinity receptor, J. Biol, Chem., vol. 277, No. 40, p. 37492-37502, 2002.

Seko, Y. et al., The role of cytokine mRNA stability in the pathogenesis of autoimmune disease, Autoimmun. Rev., vol. 5, p. 299-305, 2006.

Semenkovich, C. F. et al., A protein partially expressed on the surface of HepG2 cells that binds lipoproteins specifically is nucleolin, Biochemistry, vol. 29, p. 9708-9713, 1990.

Shun, C. T. et al., Glucosyltransferases of viridans *Streptococci* are modulins of interleukin-6 induction in infective endocarditis, Infec. Immun., vol. 73, No. 6, p. 3261-3270, 2005.

Srivastava, M. et al., Molecular dissection of nucleolin's role in growth and cell proliferation: new insights, Fasteb J., vol. 13, p. 1911-1922, 1999.

(56) References Cited

OTHER PUBLICATIONS

Zanotti et al., Cytokine modulation in sepsis and septic shock, Expert Opin. Investig. Drugs, vol. 11, p. 1061-1075, 2002.

Yip, George W., et al., "Therapeutic value of glycosaminoglycans in cancer", Mol. Cancer Ther., Sep. 2006, pp. 2139-2148.

* cited by examiner

SEQUENCE LISTING

<160> NUMBER OF SEQ ID NOS: 20

<210> SEQ ID NO 1
<211> LENGTH: 10
<212> TYPE: PRT
<213> ORGANISM: Artificial Sequence
<220> FEATURE:
<223> OTHER INFORMATION: Synthetic peptide

<400> SEQUENCE: 1

Lys Lys Lys Gly Pro Lys Glu Lys Gly Cys
1               5                   10

<210> SEQ ID NO 2
<211> LENGTH: 6
<212> TYPE: PRT
<213> ORGANISM: Artificial Sequence
<220> FEATURE:
<223> OTHER INFORMATION: Synthetic peptide

<400> SEQUENCE: 2

Lys Lys Lys Lys Gly Cys
1               5

<210> SEQ ID NO 3
<211> LENGTH: 12
<212> TYPE: PRT
<213> ORGANISM: Artificial Sequence
<220> FEATURE:
<223> OTHER INFORMATION: Synthetic peptide

<400> SEQUENCE: 3

Lys Lys Lys Lys Gly Pro Lys Lys Lys Lys Gly Ala
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (9)..(9)
<223> OTHER INFORMATION: Xaa represents (2S)-2-aminohexanamide

<400> SEQUENCE: 4

Lys Lys Lys Gly Pro Lys Glu Lys Xaa
1               5

<210> SEQ ID NO 5
<211> LENGTH: 15
<212> TYPE: PRT
<213> ORGANISM: Artificial Sequence

```
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Acetyl Lysine
<220> FEATURE:
<221> NAME/KEY: MOD_RES
<222> LOCATION: (15)..(15)
<223> OTHER INFORMATION: Amide Glycine

<400> SEQUENCE: 5

Lys Ala Lys Pro Gly Lys Ala Lys Pro Gly Lys Ala Lys Pro Gly
1               5                   10                  15

<210> SEQ ID NO 6
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Aib (2-aminoisobutyric acid)
<220> FEATURE:
<221> NAME/KEY: MOD_RES
<222> LOCATION: (3)..(3)
<223> OTHER INFORMATION: Aib (2-aminoisobutyric acid)

<400> SEQUENCE: 6

Xaa Lys Xaa Gly
1

<210> SEQ ID NO 7
<211> LENGTH: 3
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Aib (2-aminoisobutyric acid)

<400> SEQUENCE: 7

Lys Xaa Gly
1

<210> SEQ ID NO 8
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Aib (2-aminoisobutyric acid)
<220> FEATURE:
<221> NAME/KEY: MOD_RES
<222> LOCATION: (3)..(3)
<223> OTHER INFORMATION: Aib (2-aminoisobutyric acid)
<220> FEATURE:
<221> NAME/KEY: MOD_RES
<222> LOCATION: (5)..(5)
<223> OTHER INFORMATION: Aib (2-aminoisobutyric acid)
<220> FEATURE:
<221> NAME/KEY: MOD_RES
<222> LOCATION: (7)..(7)
<223> OTHER INFORMATION: Aib (2-aminoisobutyric acid)
<220> FEATURE:
<221> NAME/KEY: MOD_RES
```

<222> LOCATION: (9)..(9)
<223> OTHER INFORMATION: Aib (2-aminoisobutyric acid)
<220> FEATURE:
<221> NAME/KEY: MOD_RES
<222> LOCATION: (11)..(11)
<223> OTHER INFORMATION: Aib (2-aminoisobutyric acid)
<220> FEATURE:
<221> NAME/KEY: MOD_RES
<222> LOCATION: (13)..(13)
<223> OTHER INFORMATION: Aib (2-aminoisobutyric acid)
<220> FEATURE:
<221> NAME/KEY: MOD_RES
<222> LOCATION: (15)..(15)
<223> OTHER INFORMATION: Aib (2-aminoisobutyric acid)
<220> FEATURE:
<221> NAME/KEY: MOD_RES
<222> LOCATION: (17)..(17)
<223> OTHER INFORMATION: Aib (2-aminoisobutyric acid)
<220> FEATURE:
<221> NAME/KEY: MOD_RES
<222> LOCATION: (19)..(19)
<223> OTHER INFORMATION: Aib (2-aminoisobutyric acid)

<400> SEQUENCE: 8

Xaa Lys Xaa Gly Xaa Lys Xaa Gly Xaa Lys Xaa Gly Xaa Lys Xaa Gly
1               5                   10                  15

Xaa Lys Xaa Gly
            20

<210> SEQ ID NO 9
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: Aib (2-aminoisobutyric acid)
<220> FEATURE:
<221> NAME/KEY: MOD_RES
<222> LOCATION: (5)..(5)
<223> OTHER INFORMATION: Aib (2-aminoisobutyric acid)
<220> FEATURE:
<221> NAME/KEY: MOD_RES
<222> LOCATION: (8)..(8)
<223> OTHER INFORMATION: Aib (2-aminoisobutyric acid)
<220> FEATURE:
<221> NAME/KEY: MOD_RES
<222> LOCATION: (11)..(11)
<223> OTHER INFORMATION: Aib (2-aminoisobutyric acid)
<220> FEATURE:
<221> NAME/KEY: MOD_RES
<222> LOCATION: (14)..(14)
<223> OTHER INFORMATION: Aib (2-aminoisobutyric acid)

<400> SEQUENCE: 9

Lys Xaa Gly Lys Xaa Gly Lys Xaa Gly Lys Xaa Gly Lys Xaa Gly
1               5                   10                  15

<210> SEQ ID NO 10
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Aib (2-aminoisobutyric acid)
<220> FEATURE:
<221> NAME/KEY: MOD_RES
<222> LOCATION: (1)..(1)
<223> OTHER INFORMATION: Acetyl Lysine

```
<220> FEATURE:
<221> NAME/KEY: MOD_RES
<222> LOCATION: (3)..(3)
<223> OTHER INFORMATION: Aib (2-aminoisobutyric acid)
<220> FEATURE:
<221> NAME/KEY: MOD_RES
<222> LOCATION: (5)..(5)
<223> OTHER INFORMATION: Aib (2-aminoisobutyric acid)
<220> FEATURE:
<221> NAME/KEY: MOD_RES
<222> LOCATION: (7)..(7)
<223> OTHER INFORMATION: Aib (2-aminoisobutyric acid)
<220> FEATURE:
<221> NAME/KEY: MOD_RES
<222> LOCATION: (9)..(9)
<223> OTHER INFORMATION: Aib (2-aminoisobutyric acid)
<220> FEATURE:
<221> NAME/KEY: MOD_RES
<222> LOCATION: (11)..(11)
<223> OTHER INFORMATION: Aib (2-aminoisobutyric acid)
<220> FEATURE:
<221> NAME/KEY: MOD_RES
<222> LOCATION: (13)..(13)
<223> OTHER INFORMATION: Aib (2-aminoisobutyric acid)
<220> FEATURE:
<221> NAME/KEY: MOD_RES
<222> LOCATION: (15)..(15)
<223> OTHER INFORMATION: Aib (2-aminoisobutyric acid)
<220> FEATURE:
<221> NAME/KEY: MOD_RES
<222> LOCATION: (17)..(17)
<223> OTHER INFORMATION: Aib (2-aminoisobutyric acid)
<220> FEATURE:
<221> NAME/KEY: MOD_RES
<222> LOCATION: (19)..(19)
<223> OTHER INFORMATION: Aib (2-aminoisobutyric acid)
<220> FEATURE:
<221> NAME/KEY: MOD_RES
<222> LOCATION: (20)..(20)
<223> OTHER INFORMATION: Amide Glycine

<400> SEQUENCE: 10

Xaa Lys Xaa Gly Xaa Lys Xaa Gly Xaa Lys Xaa Gly Xaa Lys Xaa Gly
1               5                   10                  15

Xaa Lys Xaa Gly
            20

<210> SEQ ID NO 11
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Acetyl Lysine
<220> FEATURE:
<221> NAME/KEY: MOD_RES
<222> LOCATION: (2)..(2)
<223> OTHER INFORMATION: Aib (2-aminoisobutyric acid)
<220> FEATURE:
<221> NAME/KEY: MOD_RES
<222> LOCATION: (5)..(5)
<223> OTHER INFORMATION: Aib (2-aminoisobutyric acid)
<220> FEATURE:
<221> NAME/KEY: MOD_RES
<222> LOCATION: (8)..(8)
<223> OTHER INFORMATION: Aib (2-aminoisobutyric acid)
<220> FEATURE:
<221> NAME/KEY: MOD_RES
<222> LOCATION: (11)..(11)
<223> OTHER INFORMATION: Aib (2-aminoisobutyric acid)
<220> FEATURE:
<221> NAME/KEY: MOD_RES
<222> LOCATION: (14)..(14)
```

-continued

<223> OTHER INFORMATION: Aib (2-aminoisobutyric acid)
<220> FEATURE:
<221> NAME/KEY: MOD_RES
<222> LOCATION: (15)..(15)
<223> OTHER INFORMATION: Amide Glycine

<400> SEQUENCE: 11

Lys Xaa Gly Lys Xaa Gly Lys Xaa Gly Lys Xaa Gly Lys Xaa Gly
1               5                   10                  15

<210> SEQ ID NO 12
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Aib (2-aminoisobutyric acid)
<220> FEATURE:
<221> NAME/KEY: MOD_RES
<222> LOCATION: (1)..(1)
<223> OTHER INFORMATION: Acetyl Lysine
<220> FEATURE:
<221> NAME/KEY: MOD_RES
<222> LOCATION: (3)..(3)
<223> OTHER INFORMATION: Aib (2-aminoisobutyric acid)
<220> FEATURE:
<221> NAME/KEY: MOD_RES
<222> LOCATION: (5)..(5)
<223> OTHER INFORMATION: Aib (2-aminoisobutyric acid)
<220> FEATURE:
<221> NAME/KEY: MOD_RES
<222> LOCATION: (7)..(7)
<223> OTHER INFORMATION: Aib (2-aminoisobutyric acid)
<220> FEATURE:
<221> NAME/KEY: MOD_RES
<222> LOCATION: (9)..(9)
<223> OTHER INFORMATION: Aib (2-aminoisobutyric acid)
<220> FEATURE:
<221> NAME/KEY: MOD_RES
<222> LOCATION: (11)..(11)
<223> OTHER INFORMATION: Aib (2-aminoisobutyric acid)
<220> FEATURE:
<221> NAME/KEY: MOD_RES
<222> LOCATION: (13)..(13)
<223> OTHER INFORMATION: Aib (2-aminoisobutyric acid)
<220> FEATURE:
<221> NAME/KEY: MOD_RES
<222> LOCATION: (15)..(15)
<223> OTHER INFORMATION: Aib (2-aminoisobutyric acid)
<220> FEATURE:
<221> NAME/KEY: MOD_RES
<222> LOCATION: (17)..(17)
<223> OTHER INFORMATION: Aib (2-aminoisobutyric acid)
<220> FEATURE:
<221> NAME/KEY: MOD_RES
<222> LOCATION: (19)..(19)
<223> OTHER INFORMATION: Aib (2-aminoisobutyric acid)
<220> FEATURE:
<221> NAME/KEY: MOD_RES
<222> LOCATION: (21)..(21)
<223> OTHER INFORMATION: Aib (2-aminoisobutyric acid)
<220> FEATURE:
<221> NAME/KEY: MOD_RES
<222> LOCATION: (23)..(23)
<223> OTHER INFORMATION: Aib (2-aminoisobutyric acid)
<220> FEATURE:
<221> NAME/KEY: MOD_RES
<222> LOCATION: (24)..(24)
<223> OTHER INFORMATION: Amide Glycine

<400> SEQUENCE: 12

Xaa Lys Xaa Gly Xaa Lys Xaa Gly Xaa Lys Xaa Gly Xaa Lys Xaa Gly
1               5                   10                  15

```
Xaa Lys Xaa Gly Xaa Lys Xaa Gly
            20

<210> SEQ ID NO 13
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Acetyl Lysine
<220> FEATURE:
<221> NAME/KEY: MOD_RES
<222> LOCATION: (2)..(2)
<223> OTHER INFORMATION: Aib (2-aminoisobutyric acid)
<220> FEATURE:
<221> NAME/KEY: MOD_RES
<222> LOCATION: (5)..(5)
<223> OTHER INFORMATION: Aib (2-aminoisobutyric acid)
<220> FEATURE:
<221> NAME/KEY: MOD_RES
<222> LOCATION: (8)..(8)
<223> OTHER INFORMATION: Aib (2-aminoisobutyric acid)
<220> FEATURE:
<221> NAME/KEY: MOD_RES
<222> LOCATION: (11)..(11)
<223> OTHER INFORMATION: Aib (2-aminoisobutyric acid)
<220> FEATURE:
<221> NAME/KEY: MOD_RES
<222> LOCATION: (14)..(14)
<223> OTHER INFORMATION: Aib (2-aminoisobutyric acid)
<220> FEATURE:
<221> NAME/KEY: MOD_RES
<222> LOCATION: (17)..(17)
<223> OTHER INFORMATION: Aib (2-aminoisobutyric acid)
<220> FEATURE:
<221> NAME/KEY: MOD_RES
<222> LOCATION: (18)..(18)
<223> OTHER INFORMATION: Amide Glycine

<400> SEQUENCE: 13

Lys Xaa Gly Lys Xaa Gly Lys Xaa Gly Lys Xaa Gly Lys Xaa Gly Lys
1               5                   10                  15

Xaa Gly

<210> SEQ ID NO 14
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: BINDING
<222> LOCATION: (1)..(1)
<223> OTHER INFORMATION: Lysinyl proline
<220> FEATURE:
<221> NAME/KEY: BINDING
<222> LOCATION: (3)..(3)
<223> OTHER INFORMATION: N6-Arg-Pro-Lysinyl
<220> FEATURE:
<221> NAME/KEY: BINDING
<222> LOCATION: (5)..(5)
<223> OTHER INFORMATION: N6-Arg-Pro-Lysinyl
<220> FEATURE:
<221> NAME/KEY: BINDING
<222> LOCATION: (8)..(8)
<223> OTHER INFORMATION: N6-Arg-Pro-Lysinyl
<220> FEATURE:
<221> NAME/KEY: BINDING
<222> LOCATION: (10)..(10)
<223> OTHER INFORMATION: N6-Arg-Pro-Lysinyl
<220> FEATURE:
```

```
<221> NAME/KEY: MOD_RES
<222> LOCATION: (11)..(11)
<223> OTHER INFORMATION: Xaa represents (2S)-2-aminohexanamide

<400> SEQUENCE: 14

Pro Arg Lys Lys Lys Gly Pro Lys Glu Lys Xaa
1               5                   10

<210> SEQ ID NO 15
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Aib (2-aminoisobutyric acid)
<220> FEATURE:
<221> NAME/KEY: MOD_RES
<222> LOCATION: (1)..(1)
<223> OTHER INFORMATION: Acetyl Lysine
<220> FEATURE:
<221> NAME/KEY: BINDING
<222> LOCATION: (2)..(2)
<223> OTHER INFORMATION: N6-Arg-Pro-Lysinyl
<220> FEATURE:
<221> NAME/KEY: MOD_RES
<222> LOCATION: (3)..(3)
<223> OTHER INFORMATION: Aib (2-aminoisobutyric acid)
<220> FEATURE:
<221> NAME/KEY: MOD_RES
<222> LOCATION: (5)..(5)
<223> OTHER INFORMATION: Aib (2-aminoisobutyric acid)
<220> FEATURE:
<221> NAME/KEY: BINDING
<222> LOCATION: (6)..(6)
<223> OTHER INFORMATION: N6-Arg-Pro-Lysinyl
<220> FEATURE:
<221> NAME/KEY: MOD_RES
<222> LOCATION: (7)..(7)
<223> OTHER INFORMATION: Aib (2-aminoisobutyric acid)
<220> FEATURE:
<221> NAME/KEY: MOD_RES
<222> LOCATION: (9)..(9)
<223> OTHER INFORMATION: Aib (2-aminoisobutyric acid)
<220> FEATURE:
<221> NAME/KEY: BINDING
<222> LOCATION: (10)..(10)
<223> OTHER INFORMATION: N6-Arg-Pro-Lysinyl
<220> FEATURE:
<221> NAME/KEY: MOD_RES
<222> LOCATION: (11)..(11)
<223> OTHER INFORMATION: Aib (2-aminoisobutyric acid)
<220> FEATURE:
<221> NAME/KEY: MOD_RES
<222> LOCATION: (13)..(13)
<223> OTHER INFORMATION: Aib (2-aminoisobutyric acid)
<220> FEATURE:
<221> NAME/KEY: BINDING
<222> LOCATION: (14)..(14)
<223> OTHER INFORMATION: N6-Arg-Pro-Lysinyl
<220> FEATURE:
<221> NAME/KEY: MOD_RES
<222> LOCATION: (15)..(15)
<223> OTHER INFORMATION: Aib (2-aminoisobutyric acid)
<220> FEATURE:
<221> NAME/KEY: MOD_RES
<222> LOCATION: (17)..(17)
<223> OTHER INFORMATION: Aib (2-aminoisobutyric acid)
<220> FEATURE:
<221> NAME/KEY: BINDING
<222> LOCATION: (18)..(18)
<223> OTHER INFORMATION: N6-Arg-Pro-Lysinyl
<220> FEATURE:
<221> NAME/KEY: MOD_RES
<222> LOCATION: (19)..(19)
```

```
<223> OTHER INFORMATION: Aib (2-aminoisobutyric acid)
<220> FEATURE:
<221> NAME/KEY: MOD_RES
<222> LOCATION: (20)..(20)
<223> OTHER INFORMATION: Amide Glysine

<400> SEQUENCE: 15

Xaa Lys Xaa Gly Xaa Lys Xaa Gly Xaa Lys Xaa Gly Xaa Lys Xaa Gly
1               5                   10                  15

Xaa Lys Xaa Gly
            20

<210> SEQ ID NO 16
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Acetyl Lysine
<220> FEATURE:
<221> NAME/KEY: BINDING
<222> LOCATION: (1)..(1)
<223> OTHER INFORMATION: N6-Arg-Pro-Lysinyl
<220> FEATURE:
<221> NAME/KEY: MOD_RES
<222> LOCATION: (2)..(2)
<223> OTHER INFORMATION: Aib (2-aminoisobutyric acid)
<220> FEATURE:
<221> NAME/KEY: BINDING
<222> LOCATION: (4)..(4)
<223> OTHER INFORMATION: N6-Arg-Pro-Lysinyl
<220> FEATURE:
<221> NAME/KEY: MOD_RES
<222> LOCATION: (5)..(5)
<223> OTHER INFORMATION: Aib (2-aminoisobutyric acid)
<220> FEATURE:
<221> NAME/KEY: BINDING
<222> LOCATION: (7)..(7)
<223> OTHER INFORMATION: N6-Arg-Pro-Lysinyl
<220> FEATURE:
<221> NAME/KEY: MOD_RES
<222> LOCATION: (8)..(8)
<223> OTHER INFORMATION: Aib (2-aminoisobutyric acid)
<220> FEATURE:
<221> NAME/KEY: BINDING
<222> LOCATION: (10)..(10)
<223> OTHER INFORMATION: N6-Arg-Pro-Lysinyl
<220> FEATURE:
<221> NAME/KEY: MOD_RES
<222> LOCATION: (11)..(11)
<223> OTHER INFORMATION: Aib (2-aminoisobutyric acid)
<220> FEATURE:
<221> NAME/KEY: BINDING
<222> LOCATION: (13)..(13)
<223> OTHER INFORMATION: N6-Arg-Pro-Lysinyl
<220> FEATURE:
<221> NAME/KEY: MOD_RES
<222> LOCATION: (14)..(14)
<223> OTHER INFORMATION: Aib (2-aminoisobutyric acid)
<220> FEATURE:
<221> NAME/KEY: MOD_RES
<222> LOCATION: (15)..(15)
<223> OTHER INFORMATION: Amide Glycine

<400> SEQUENCE: 16

Lys Xaa Gly Lys Xaa Gly Lys Xaa Gly Lys Xaa Gly Lys Xaa Gly
1               5                   10                  15

<210> SEQ ID NO 17
<211> LENGTH: 18
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Acetyl Lysine
<220> FEATURE:
<221> NAME/KEY: BINDING
<222> LOCATION: (1)..(1)
<223> OTHER INFORMATION: N6-Arg-Pro-Lysinyl
<220> FEATURE:
<221> NAME/KEY: MOD_RES
<222> LOCATION: (2)..(2)
<223> OTHER INFORMATION: Aib (2-aminoisobutyric acid)
<220> FEATURE:
<221> NAME/KEY: BINDING
<222> LOCATION: (4)..(4)
<223> OTHER INFORMATION: Lys-X-Pro-Arg-Lys. X represente la liaison
      (-CH2NH-)
<220> FEATURE:
<221> NAME/KEY: MOD_RES
<222> LOCATION: (5)..(5)
<223> OTHER INFORMATION: Aib (2-aminoisobutyric acid)
<220> FEATURE:
<221> NAME/KEY: BINDING
<222> LOCATION: (7)..(7)
<223> OTHER INFORMATION: N6-Arg-Pro-Lysinyl
<220> FEATURE:
<221> NAME/KEY: MOD_RES
<222> LOCATION: (8)..(8)
<223> OTHER INFORMATION: Aib (2-aminoisobutyric acid)
<220> FEATURE:
<221> NAME/KEY: BINDING
<222> LOCATION: (10)..(10)
<223> OTHER INFORMATION: N6-Arg-Pro-Lysinyl
<220> FEATURE:
<221> NAME/KEY: MOD_RES
<222> LOCATION: (11)..(11)
<223> OTHER INFORMATION: Aib (2-aminoisobutyric acid)
<220> FEATURE:
<221> NAME/KEY: BINDING
<222> LOCATION: (13)..(13)
<223> OTHER INFORMATION: N6-Arg-Pro-Lysinyl
<220> FEATURE:
<221> NAME/KEY: MOD_RES
<222> LOCATION: (14)..(14)
<223> OTHER INFORMATION: Aib (2-aminoisobutyric acid)
<220> FEATURE:
<221> NAME/KEY: BINDING
<222> LOCATION: (16)..(16)
<223> OTHER INFORMATION: N6-Arg-Pro-Lysinyl
<220> FEATURE:
<221> NAME/KEY: MOD_RES
<222> LOCATION: (17)..(17)
<223> OTHER INFORMATION: Aib (2-aminoisobutyric acid)
<220> FEATURE:
<221> NAME/KEY: MOD_RES
<222> LOCATION: (18)..(18)
<223> OTHER INFORMATION: Amide Glycine

<400> SEQUENCE: 17

Lys Xaa Gly Lys Xaa Gly Lys Xaa Gly Lys Xaa Gly Lys Xaa Gly Lys
1               5                   10                  15

Xaa Gly

<210> SEQ ID NO 18
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Acetyl Lysine
```

-continued

```
<220> FEATURE:
<221> NAME/KEY: BINDING
<222> LOCATION: (1)..(1)
<223> OTHER INFORMATION: N6-Arg-Pro-Lysinyl
<220> FEATURE:
<221> NAME/KEY: BINDING
<222> LOCATION: (3)..(3)
<223> OTHER INFORMATION: N6-Arg-Pro-Lysinyl
<220> FEATURE:
<221> NAME/KEY: BINDING
<222> LOCATION: (6)..(6)
<223> OTHER INFORMATION: N6-Arg-Pro-Lysinyl
<220> FEATURE:
<221> NAME/KEY: BINDING
<222> LOCATION: (8)..(8)
<223> OTHER INFORMATION: N6-Arg-Pro-Lysinyl
<220> FEATURE:
<221> NAME/KEY: BINDING
<222> LOCATION: (11)..(11)
<223> OTHER INFORMATION: N6-Arg-Pro-Lysinyl
<220> FEATURE:
<221> NAME/KEY: BINDING
<222> LOCATION: (13)..(13)
<223> OTHER INFORMATION: N6-Arg-Pro-Lysinyl
<220> FEATURE:
<221> NAME/KEY: MOD_RES
<222> LOCATION: (15)..(15)
<223> OTHER INFORMATION: Amide Glycine

<400> SEQUENCE: 18

Lys Ala Lys Pro Gly Lys Ala Lys Pro Gly Lys Ala Lys Pro Gly
1               5                   10                  15

<210> SEQ ID NO 19
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Acetyl Lysine
<220> FEATURE:
<221> NAME/KEY: BINDING
<222> LOCATION: (1)..(1)
<223> OTHER INFORMATION: N6-Arg-Pro-Lysinyl
<220> FEATURE:
<221> NAME/KEY: MOD_RES
<222> LOCATION: (2)..(2)
<223> OTHER INFORMATION: Aib (2-aminoisobutyric acid)
<220> FEATURE:
<221> NAME/KEY: BINDING
<222> LOCATION: (4)..(4)
<223> OTHER INFORMATION: N6-Arg-Pro-Lysinyl
<220> FEATURE:
<221> NAME/KEY: MOD_RES
<222> LOCATION: (5)..(5)
<223> OTHER INFORMATION: Aib (2-aminoisobutyric acid)
<220> FEATURE:
<221> NAME/KEY: BINDING
<222> LOCATION: (7)..(7)
<223> OTHER INFORMATION: N6-Arg-Pro-Lysinyl
<220> FEATURE:
<221> NAME/KEY: MOD_RES
<222> LOCATION: (8)..(8)
<223> OTHER INFORMATION: Aib (2-aminoisobutyric acid)
<220> FEATURE:
<221> NAME/KEY: BINDING
<222> LOCATION: (10)..(10)
<223> OTHER INFORMATION: N6-Arg-Pro-Lysinyl
```

```
<220> FEATURE:
<221> NAME/KEY: MOD_RES
<222> LOCATION: (11)..(11)
<223> OTHER INFORMATION: Aib (2-aminoisobutyric acid)
<220> FEATURE:
<221> NAME/KEY: MOD_RES
<222> LOCATION: (12)..(12)
<223> OTHER INFORMATION: Amide Glycine

<400> SEQUENCE: 19

Lys Xaa Gly Lys Xaa Gly Lys Xaa Gly Lys Xaa Gly
1               5                   10

<210> SEQ ID NO 20
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Acetyl Lysine
<220> FEATURE:
<221> NAME/KEY: BINDING
<222> LOCATION: (1)..(1)
<223> OTHER INFORMATION: N6-Arg-Pro-Lysinyl
<220> FEATURE:
<221> NAME/KEY: MOD_RES
<222> LOCATION: (2)..(2)
<223> OTHER INFORMATION: Aib (2-aminoisobutyric acid)
<220> FEATURE:
<221> NAME/KEY: BINDING
<222> LOCATION: (4)..(4)
<223> OTHER INFORMATION: Lys-X-Pro-Arg-Lys. X represents la liaison
      (-CH2NH-)
<220> FEATURE:
<221> NAME/KEY: MOD_RES
<222> LOCATION: (5)..(5)
<223> OTHER INFORMATION: Aib (2-aminoisobutyric acid)
<220> FEATURE:
<221> NAME/KEY: BINDING
<222> LOCATION: (7)..(7)
<223> OTHER INFORMATION: N6-Arg-Pro-Lysinyl
<220> FEATURE:
<221> NAME/KEY: MOD_RES
<222> LOCATION: (8)..(8)
<223> OTHER INFORMATION: Aib (2-aminoisobutyric acid)
<220> FEATURE:
<221> NAME/KEY: BINDING
<222> LOCATION: (10)..(10)
<223> OTHER INFORMATION: N6-Arg-Pro-Lysinyl
<220> FEATURE:
<221> NAME/KEY: MOD_RES
<222> LOCATION: (11)..(11)
<223> OTHER INFORMATION: Aib (2-aminoisobutyric acid)
<220> FEATURE:
<221> NAME/KEY: BINDING
<222> LOCATION: (13)..(13)
<223> OTHER INFORMATION: N6-Arg-Pro-Lysinyl
<220> FEATURE:
<221> NAME/KEY: MOD_RES
<222> LOCATION: (14)..(14)
<223> OTHER INFORMATION: Aib (2-aminoisobutyric acid)
```

-continued

```
<220> FEATURE:
<221> NAME/KEY: BINDING
<222> LOCATION: (16)..(16)
<223> OTHER INFORMATION: N6-Arg-Pro-Lysinyl
<220> FEATURE:
<221> NAME/KEY: MOD_RES
<222> LOCATION: (17)..(17)
<223> OTHER INFORMATION: Aib (2-aminoisobutyric acid)
<220> FEATURE:
<221> NAME/KEY: BINDING
<222> LOCATION: (19)..(19)
<223> OTHER INFORMATION: N6-Arg-Pro-Lysinyl
<220> FEATURE:
<221> NAME/KEY: MOD_RES
<222> LOCATION: (20)..(20)
<223> OTHER INFORMATION: Aib (2-aminoisobutyric acid)
<220> FEATURE:
<221> NAME/KEY: BINDING
<222> LOCATION: (22)..(22)
<223> OTHER INFORMATION: N6-Arg-Pro-Lysinyl
<220> FEATURE:
<221> NAME/KEY: MOD_RES
<222> LOCATION: (23)..(23)
<223> OTHER INFORMATION: Aib (2-aminoisobutyric acid)
<220> FEATURE:
<221> NAME/KEY: MOD_RES
<222> LOCATION: (24)..(24)
<223> OTHER INFORMATION: Amide Glycine

<400> SEQUENCE: 20

Lys Xaa Gly Lys Xaa Gly Lys Xaa Gly Lys Xaa Gly Lys Xaa Gly Lys
1               5                   10                  15

Xaa Gly Lys Xaa Gly Lys Xaa Gly
            20
```

OPTICALLY PURE COMPOUNDS FOR IMPROVED THERAPEUTIC EFFICIENCY

This application is a national stage of PCT International Application No. PCT/IB2008/053469, filed May 22, 2008, the entire disclosure of which is herein expressly incorporated by reference.

TECHNICAL FIELD OF THE INVENTION

The present invention relates to new optically pure compounds displaying an improved anticancer activity compared to previously known complex mixtures of stereoisomers thereof. Such compounds are of formula (I):

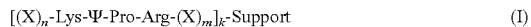

$$[(X)_n\text{-Lys-}\Psi\text{-Pro-Arg-}(X)_m]_k\text{-Support} \quad (I)$$

wherein each X independently represents any amino acid; n is 0 or 1; m is an integer between 0 and 3; k is an integer of at least 3; Ψ is a reduced bond of formula (—CH$_2$N—) replacing the peptide amide bond between Lys and Pro; and wherein Lys residues in [(X)$_n$-Lys-Ψ-Pro-Arg-(X)$_m$] pseudopeptide units of said compound of formula (I) are either all in L configuration or all in D configuration. A method for preparing such compounds and therapeutic uses thereof are also provided.

BACKGROUND ART

Cell division, or mitosis, is the process which allows cells to multiply in order to repair or regenerate tissues and replace dead cells. In cancer cells, regulation of this process is defective and this is why these cells divide anarchically and give rise to tumours. Thus, one effective therapeutic route to prevent the development of cancer consists in blocking the division of cancerous cells using molecules with anti-mitotic properties.

In addition, every tumor needs nutrients and oxygen in order to grow. These elements are provided by intratumoral blood vessels which result from a mechanism known as angiogenesis. In fact, if these vessels are absent, tumour cells undergo a cell necrosis process, and tumour growth slows down then stops. An example of another therapeutic route to combat cancer therefore consists in blocking the angiogenesis process by blocking the molecules controlling this mechanism.

It would therefore be extremely useful to have available new anti-cancer molecules capable of inhibiting both tumour cell proliferation and the angiogenesis process in the tumour.

Moreover, the majority of current anti-cancer agents are not truly specific to tumour cells and therefore also target healthy cells, thus giving rise to many, and at times serious, side effects.

Still another problem linked to conventional anti-cancer drugs, such as paclitaxel, is that these molecules are often highly hydrophobic which makes it necessary to develop complicated and expensive pharmaceutical formulations in order to achieve acceptable bio availability in vivo. The problem of in vivo bioavailability is all the more acute in the case of treatment using nucleic acids since it is extremely difficult for them to reach their target cells in an efficacious and specific manner.

It would therefore be extremely useful to have available new anti-cancer molecules which present the following characteristics:

much improved efficacy as a result of their dual inhibitory action on tumour proliferation and angiogenesis such that they can be effective alone, without the use of conventional chemotherapy or radiotherapy and thus greatly the limit side effects linked to these types of treatment, a fairly broad spectrum of activity against angiogenic factors to prevent resistance to treatment, very few side effects as a result of greater specificity towards tumour cells, a synthesis process that is easily adaptable to an industrial scale, easier to use, notably as a result of better bioavailability and/or longer half-life in vivo, in particular as a result of direct specificity for tumour cells, with good solubility in aqueous media and improved resistance to in vivo breakdown processes.

WO2007/125210 (1), the whole content of which is herein incorporated by reference, discloses promising compounds useful notably for cancer treatment.

These compounds display several advantageous properties:

they are capable of having high anti-tumour efficacy alone as a result of a dual effect on tumour proliferation and angiogenesis, efficacy that makes it possible to envisage a single treatment without being combined with a conventional chemotherapy molecule such as taxol;

they do not have specificity for a particular type of cancer but rather a broad spectrum of activity against tumour cells and activated endothelial cells;

they have very few side effects in vivo as a result of specificity for tumour cells and activated endothelial cells compared to healthy cells;

they have a synthesis process that can be easily adapted to an industrial scale; and they have sufficient bioavailability in vivo in order not to require the development of particular pharmaceutical forms.

These compounds are thus very interesting since they combine many advantages necessary for the development of a new, simpler, cheaper and efficient anticancer treatment. They were also found to be good candidates for the development of new, simpler, cheaper and efficient anti-inflammatory agents.

However, it is always necessary to improve the antitumor efficiency of existing compounds. It would thus be very useful to find optimized compounds with a higher efficiency but keeping all the other advantages of these promising compounds.

The compounds of WO2007/125210 are new pseudopeptide compounds consisting of a support to which at least three pseudopeptide units are coupled. Such compounds bind surface nucleolin and display anticancer (anti-angiogenic and anti-mitotic) and anti-inflammatory activities.

It is believed that these compounds act by the interaction of the at least 3 pseudopeptide units grafted on the support with the RGG domain of surface nucleolin.

Preferred compounds have a peptide support, in particular a linear peptide support with a helicoidal structure, to which at least 3 [Lys-Ψ-Pro-Arg] (also named KΨPR) units are coupled.

In this document, a conventional method was used for preparing the KΨPR units, as described in US20040002457A1 (2) and Nisole et al (3). In such a conventional method Proline derivative which contains a secondary amine reacts with the Boc-Lys(Boc)-CHO (aldehyde) to form an enamine with partial loss of chirality at the Lys residue (5-10%). Thus, at the end of such a conventional reaction, the reaction mixture comprises 90-95% L-Lys-Ψ-Pro-Arg units and 5-10% D-Lys-Ψ-Pro-Arg units.

As a result, when this mixture is used for coupling onto the ε amino groups of the lateral chain of the Lys residues of the support peptide, a mixture of stereoisomers is obtained. Since each Lys-Ψ-Pro-Arg unit may have either a L or D lysine, the number of stereoisomers that are obtained increases exponentially with the number of KΨPR units. For preferred compounds with 5 or 6 units, the number of obtainable stereoisomers is 32 and 64 respectively.

Similarly, performing the reductive amination step directly on-resin by reaction with Boc-Lys(Boc)-CHO with the secondary amines of pro line residues grafted on a solid support in the presence of an hydride reagent also results in the production of a mixture of stereisomers.

Using this conventional method, the obtained pseudopeptide compound is not optically pure but in contrast is composed of a very complex mixture of stereoisomers, which cannot be isolated or purified due to the mixture complexity. Indeed, the mixture is composed of a too high number of very close stereoisomers, which cannot thus be each isolated by usual purification technologies. Individual steroisomers of the compounds of interest cannot thus be purified from the complex mixture obtained using the conventional method for preparing these compounds.

The inventors have used a new method for preparing the KΨP dipeptide, which permits to obtain an optically pure L-Lys-Ψ-Pro or D-Lys-Ψ-Pro compound. This method has been adapted from the article by Cushman et al (4), which described an epimerisation effect when preparing Phe-Ψ-Pro dipeptides using the conventional method and a new method for the preparation of pure L-Phe-Ψ-Pro dipeptides.

The inventors then prepared optically pure compounds consisting of a linear support peptide to which at least 3 L-Lys-Ψ-Pro-Arg or D-Lys-Ψ-Pro-Arg units are coupled. In such optically pure compounds, the lysine residues of the various Lys-Ψ-Pro-Arg units are either all in L configuration or all in D configuration.

Surprisingly, they found that these optically pure compounds display a significantly higher anticancer efficiency than a composition comprising a mixture of stereoisomers of the same compounds.

DESCRIPTION OF THE INVENTION

The present invention thus relates to a compound of formula (I):

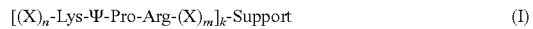

[(X)$_n$-Lys-Ψ-Pro-Arg-(X)$_m$]$_k$-Support        (I)

wherein
each X independently represents any amino acid;
n is 0 or 1;
m is an integer between 0 and 3;
k is an integer of at least 3;
Ψ is a reduced bond of formula (—CH$_2$N—) replacing the peptide amide bond between Lys and Pro; and
wherein Lys residues in [(X)$_n$-Lys-Ψ-Pro-Arg-(X)$_m$] pseudopeptide units of said compound of formula (I) are either all in L configuration or all in D configuration.

In the context of the invention, the term "support" refers to any pharmaceutically acceptable molecule, in other words without intrinsic toxicity, on which at least 3 pseudopeptide units of formula (I) can be grafted. An acceptable support therefore has to be of sufficient size to allow at least 3 pseudopeptide units of formula (I) to be grafted on it, preferably 3 to 8 pseudopeptide units of formula (I). Such an acceptable support should also preferably be large enough to allow at least 3, preferably 3 to 8, pseudopeptide units of formula (I) can come together to interact in the RGG domain of one or more nucleolin molecules. In addition, the support must not be immunogenic.

Such a support can notably be selected from a linear peptide, a peptoid (N-substituted glycine oligomer) that is linear or cyclic, a foldamer (oligomer or polymer with a strong tendency to adopt a compact, well-defined and predictable conformation in solution), a linear polymer or a spherical dendrimer (macromolecule consisting of polymers/oligomers which combine according to a tree like process around a multifunctional central core), a sugar or a nanoparticle.

Advantageously, said support is a linear peptide. The use of a linear peptide indeed allows the support to be synthesised easily.

A linear peptide acting as a support in the invention can advantageously contain a proportion of lysine greater than 25%. More precisely, when a linear peptide is used as a support in the invention, the pseudopeptide units are preferably grafted in position ε of lysine. When a linear peptide is used as the support in the invention, it therefore preferably includes at least as many lysine as the number of pseudopeptide units which are to be grafted on. Thus, in a preferred embodiment of the invention, the support is a linear peptide comprising at least k Lys residues.

In the context of the invention, the term "grafted" for the pseudopeptide units means being bound to the support by means of a covalent bond, either directly or through the intermediate of a spacer compound between the pseudopeptide and support. As a result of this, in one particular embodiment, the pseudopeptide units are grafted directly on the support without a spacer compound between them and the support. In another embodiment, the pseudopeptide units are grafted on the support through the intermediate of a spacer. Examples of acceptable spacers include compounds of the type ethylene glycol, piperazine or an amino acid of the type aminohexanoic acid or beta-alanine.

In the case where the support is a linear or cyclic peptide and where the pseudopeptide units are grafted directly on the peptide, bonding between the peptide and the pseudopeptide units is preferably carried out at the lysine residue of the peptide support, at the amino group in the α or β position, preferably at the amino group in the ε position (on the side chain) of lysine. Thus, direct grafting of pseudopeptide units on the peptide support is advantageously carried out by means of an amide bond between the acid group COOH of the amino acid in the C-terminal position of the pseudopeptide unit and an amino group of the lysine residue, preferably the amino group in the ε position (on the side chain) of lysine.

Suitable linear support peptides include those having a sequence selected from the group consisting of Lys-Lys-Lys-Gly-Pro-Lys-Glu-Lys-Gly-Cys (SEQ ID NO: 1), Lys-Lys-Lys-Lys-Gly-Cys (SEQ ID NO: 2), Lys-Lys-Lys-Lys-Gly-Pro-Lys-Lys-Lys-Gly-Ala (SEQ ID NO: 3), Lys-Lys-Gly-Pro-Lys-Glu-Lys-AhxCONH$_2$ (SEQ ID NO: 4), and Ac-Lys-Ala-Lys-Pro-Gly-Lys-Ala-Lys-Pro-Gly-Lys-Ala-Lys-Pro-Gly-CONH$_2$ (SEQ ID NO: 5), wherein "AhxCONH$_2$" represents hexanoic amino acid and CONH$_2$ represents the fact that the acid group is replaced by an amide group, AhxCONH$_2$, representing (2S)-2-aminohexanamide.

Among the linear peptides, some are known to adopt a helicoidal structure. In a preferred embodiment, the linear support peptide displays such a helicoidal structure. Indeed, thanks to the helicoidal structure, the KΨPR pseudopeptide units are very regularly presented, which might be useful for binding to the repetitive RGG domain of surface nucleolin.

Such linear support peptide with a helicoidal structure include peptides comprising at least 3, preferably between 3 and 20, preferably between 3 and 15, more preferably between 3 and 12, more preferably still between 3 and 10, even more preferably between 3 to 8, most preferably 5 or 6, units of sequence Aib-Lys-Aib-Gly (SEQ ID NO: 6) or Lys-Aib-Gly (SEQ ID NO: 7), wherein Aib is α-aminoisobutyric acid.

In advantageous embodiments, said helicoidal linear support peptide is constituted of a sequence selected from the group consisting of Aib-Lys-Aib-Gly-Aib-Lys-Aib-Gly-Aib-Lys-Aib-Gly-Aib-Lys-Aib-Gly-Aib-Lys-Aib-Gly (SEQ ID NO: 8), Lys-Aib-Gly-Lys-Aib-Gly-Lys-Aib-Gly-Lys-Aib-Gly-Lys-Aib-Gly (SEQ ID NO: 9), Ac-Aib-Lys-Aib-Gly-Aib-Lys-Aib-Gly-Aib-Lys-Aib-Gly-Aib-Lys-Aib-Gly-Aib-Lys-Aib-Gly-CONH$_2$ (SEQ ID NO: 10), Ac-Lys-Aib-Gly-Lys-Aib-Gly-Lys-Aib-Gly-Lys-Aib-Gly-Lys-Aib-Gly-CONH$_2$ (SEQ ID NO: 11), Ac-Aib-Lys-Aib-Gly-Aib-Lys-Aib-Gly-Aib-Lys-Aib-Gly-Aib-Lys-Aib-Gly-Aib-Lys-Aib-Gly-Aib-Lys-Aib-Gly-CONH$_2$ (SEQ ID NO: 12), or Ac-Lys-Aib-Gly-Lys-Aib-Gly-Lys-Aib-Gly-Lys-Aib-Gly-Lys-Aib-Gly-Lys-Aib-Gly-CONH$_2$ (SEQ ID NO: 13), wherein "Ac" represents an acetyl group, and any "amino acid-CONH$_2$" represents said amino acid in which the OH group of the COOH acid function is replaced by a NH$_2$ group, thus resulting in an amide CONH$_2$ function instead of the acid COOH function.

In the compounds of the invention, the pseudopeptide unit that is essential for binding to the RGG domain of nucleolin is the sub-unit of formula (II):

Lys-Ψ-Pro-Arg    (II).

Nevertheless, the presence at one or the other end of this essential sub-unit consisting of several amino acids as defined above is not such that it would prevent binding to nucleolin. This is why the essential sub-unit of formula (II) can include at one and/or the other end 0 to 3 of any amino acids represented in the formula (I) by (X)n and (X)m respectively, where n is equal to 0 or 1 and m is an integer between 0 and 3. Advantageously, the number of the amino acids present at one and/or other end of the essential sub-unit of formula (II) is low, in other words, n is advantageously 0 and m is advantageously an integer between 0 and 2, advantageously 0 or 1, advantageously 0. Thus in an advantageous embodiment, n and m are equal to 0.

In the context of the invention, the term "any amino acid" means any natural or synthetic amino acid, possibly modified by the presence of one or more substituents. More precisely the term amino acid means an alpha aminated amino acid with the following general structure:

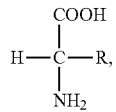

where R represents the side chain of the amino acid. In the context of the invention, R therefore represents the side chain of a natural or non-natural amino acid. The term "natural amino acid" means any amino acid which is found naturally in vivo in a living being. Natural amino acids therefore include amino acids coded by mRNA incorporated into proteins during translation but also other amino acids found naturally in vivo which are a product or by-product of a metabolic process, such as for example ornithine which is generated by the urea production process by arginase from L-arginine. In the invention, the amino acids used can therefore be natural or not. Namely, natural amino acids generally have the L configuration but also, according to the invention, an amino acid can have the L or D configuration. Moreover, R is of course not limited to the side chains of natural amino acid but can be freely chosen.

In the compounds according to the invention, at least 3 pseudopeptide units are grafted on the support. Indeed, the results obtained with non optically pure compounds in WO2007/125210 show the importance of binding to the RGG domain of nucleolin for the exceptional anti-tumor efficacy of these compounds. Binding to the RGG domain of nucleolin is obtained by means of multivalent presentation of several pseudopeptide units such as those incorporated into formula (I). In particular, it has been shown that below 3 units (k<3), the efficacy of binding to nucleolin is lower and anti-tumour efficacy is probably less. The compounds according to the invention therefore include at least 3 pseudopeptide units grafted on the support, k being an integer greater than or equal to 3. The compounds according to the invention advantageously present 3-20 (3≤k≤20), preferably 3-15, preferably 3-12, more preferably 3-10, still more preferably 3-8 pseudopeptide units grafted on the support. Moreover, the inventors have shown that activity was optimal with 5 or 6 pseudopeptide units grafted on the support (k=5), since the efficacy of binding to nucleolin does not increase with a higher number of pseudopeptide units. Advantageously, in the compounds of formula (I), k is therefore at least 3, preferably between 3 and 20, preferably between 3 and 15, preferably between 3 and 12, more preferably between 3 and 10, preferably between 3 and 8, still more preferably between 4 and 7, between 4 and 6, between 4 and 5, or between 5 and 6. Even more advantageously, in compounds of formula (I), k is equal to 5 or 6.

In normal peptide units, amino acids are linked through an amide bond of formula (—CONH—). Such a bond is sensitive to the action of proteases. The term "protease", also known as "peptidase" or "proteolytic enzyme", means any enzyme which cleaves the standard peptide bonds in proteins. This process is known as proteolytic cleavage. This involves the use of a water molecule which is what leads to proteases being classified as hydrolases. The proteases namely include proteases known as N-peptidases which carry out the cleavage of the N-terminal end of proteins. These proteases are particularly inconvenient in terms of the in vivo stability of peptides without modified peptide bonds. This is why pseudopeptide units of the compounds of formula (I) include a reduced Ψ of formula (—CH$_2$N—) between Lys and Pro so that the resistance of the sub-unit of formula Lys-Ψ-Pro-Arg (II), which is essential for binding to nucleolin, is significantly increased to these N-peptidases. This makes it possible to significantly increase the half-life of compounds of formula (I) in vivo and in vitro. The presence of a reduced Ψ bond between the lysine and proline residues is thus very important.

Although only the Ψ bond between Lys and Pro in pseudopeptide units is systematically present in compounds of formula (I), it is also possible that other peptide bonds of the pseudopeptide units may be modified to obtain a bond that is significantly more resistant to at least one protease than a standard peptide bond of formula (—CONH—). Such bonds include the Y bond of formula (—CH$_2$N—) (or (—CH$_2$NH—) if the amino acid displays a primary amino group, contrary to proline), but also other modified bonds such as a retro-inverso bond (—NHCO—), a methyleneoxy bond (—CH$_2$—O—), a thiomethylene (—CH$_2$—S—), a carba bond (—CH$_2$—CH$_2$—), a ketomethylene bond (—CO—CH$_2$—), a hydroxyethylene bond (—CHOH—CH$_2$—), a (—N—N—) bond, an E-alkene bond or a (—CH=CH—) bond. The presence of additional modified bonds may make it possible to further increase resistance to proteases of compounds of formula (I). Nevertheless, the increase linked to the presence of the first Ψ bond between Lys and Pro is already highly significant and the addition of other modified bonds complicates synthesis of the pseudopeptide units and are therefore possible but not preferred.

Indeed, as mentioned in the introduction, the classical synthesis procedure of KΨPR units used in WO2007/125210 results in a final complex reaction mixture comprising 90-95% L-Lys-Ψ-Pro-Arg units (i.e. units in which the lysine residue is in the usual L configuration) and 5-10% D-Lys-Ψ-Pro-Arg units (i.e. units in which the lysine residue is in D configuration). As a result, when this mixture is used for coupling onto the ε amino groups of the lateral chain of the Lys residues of a support peptide, a complex mixture of non-separable stereoisomers is obtained.

In contrast, using a new method described in the present application, the inventors were able to synthesize optically pure compounds, in which Lys residues in [(X)$_n$-Lys-Ψ-Pro-Arg-(X)$_m$] pseudopeptide units of the compound of formula (I) are either all in L configuration or all in D configuration.

As mentioned before, an amino acid is defined as an alpha aminated amino acid with the following general structure:

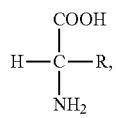

where R represents the side chain of the amino acid.

With the exception of glycine, whose side chain R is H, all amino acids have a chiral center and may thus exist as two distinct enantiomers, named L and D. The "L" and "D" configurations are related to the levogyre and dextrogyre configurations, not of the amino acids themselves, but of the corresponding glyceraldehyde. To determine if an amino acid is in L or D configuration, the absolute configuration of the corresponding glyceraldehyde is analyzed: if it corresponds to the L form of glyceraldehyde, then the amino acid is called L-amino acid, if it corresponds to the D form of glyceraldehyde, then the amino acid is called D-amino acid. For a particular amino acid, the corresponding glyceraldehyde is as follows:

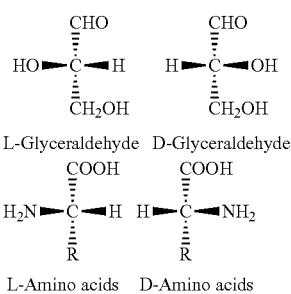

In particular, for a lysine residue, the L and D configurations can be represented as follows:

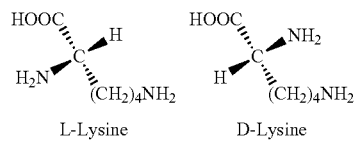

Natural amino acids are in L configuration. In particular, all amino acids in compounds of formula (I) (either in the support or in the [(X)$_n$-Lys-Ψ-Pro-Arg-(X)$_m$] pseudopeptide units) other than the lysine residues of the [(X)$_n$-Lys-Ψ-Pro-Arg-(X)$_m$] pseudopeptide units are in L configuration.

As a result, in compounds of formula (I), the [(X)$_n$-Lys-Ψ-Pro-Arg-(X)$_m$] pseudopeptide units are all of the same following formula:

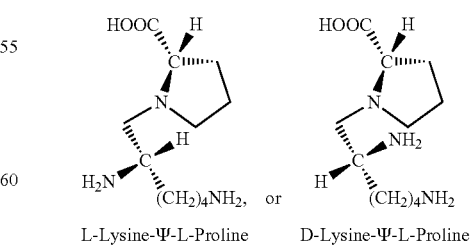

In an advantageous embodiment of an optically pure compound according to the invention, said compound is selected from the group consisting of:

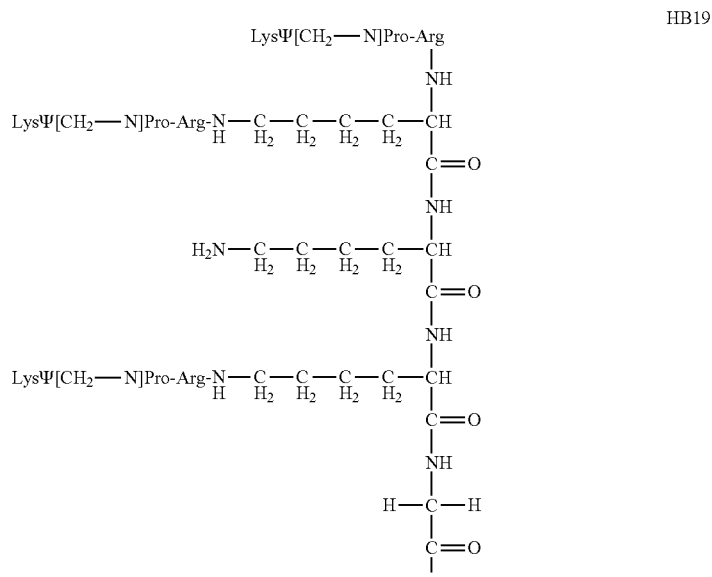
HB19
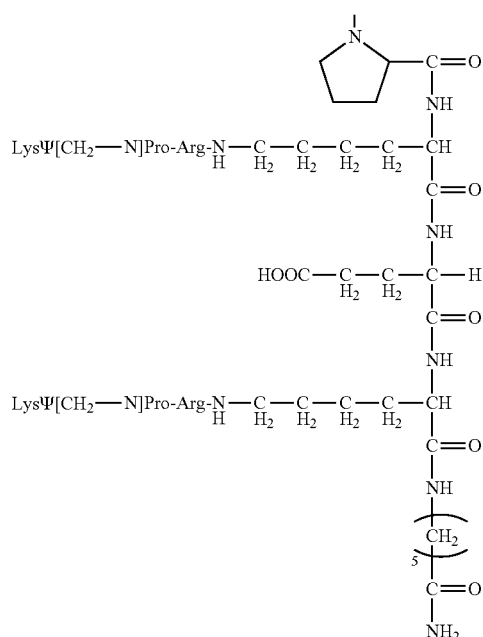
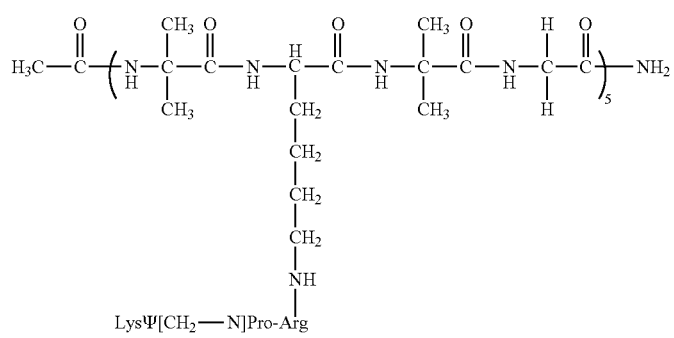
Nucant 2

-continued
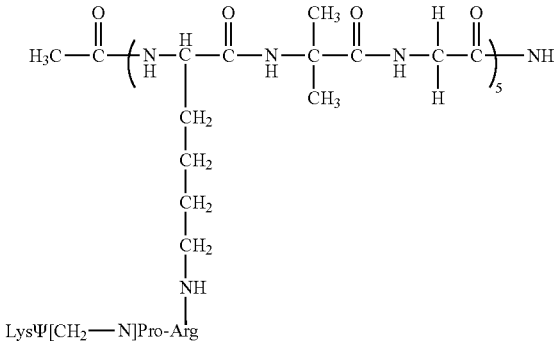
Nucant 3
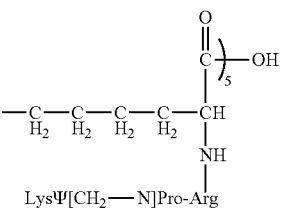
Nucant 4
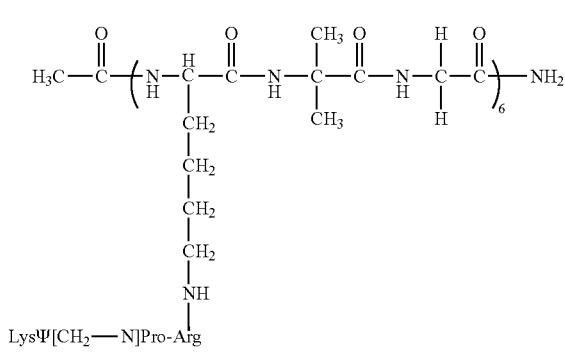
Nucant 6
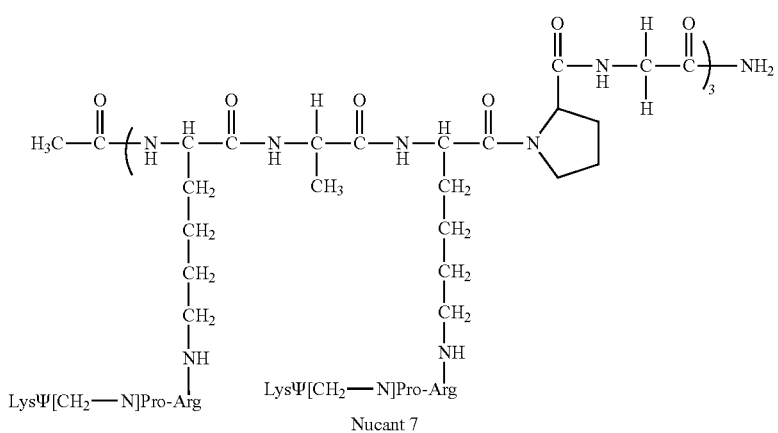
Nucant 7
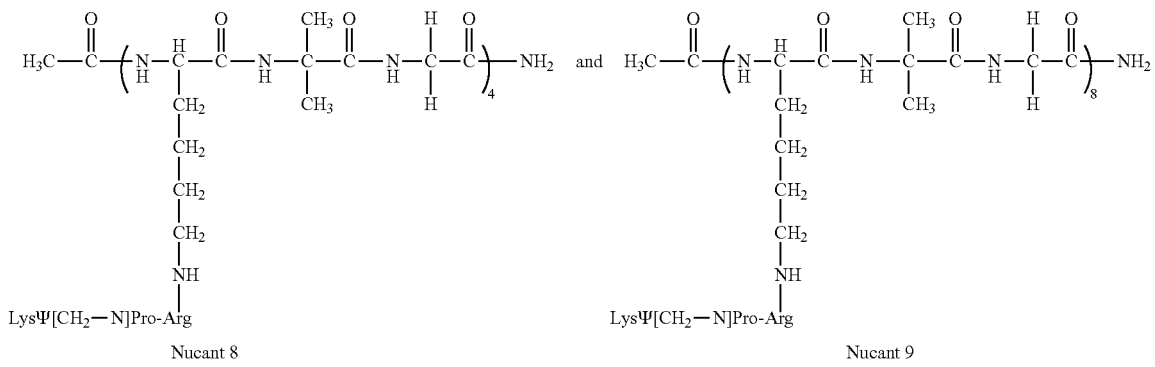
Nucant 8 and Nucant 9 wherein Lys residues in $[(X)_n\text{-Lys-}\Psi\text{-Pro-Arg-}(X)_m]$ units of formula (I) are either all in L configuration or all in D configuration.
Advantageously, said compound is selected from the group consisting of:
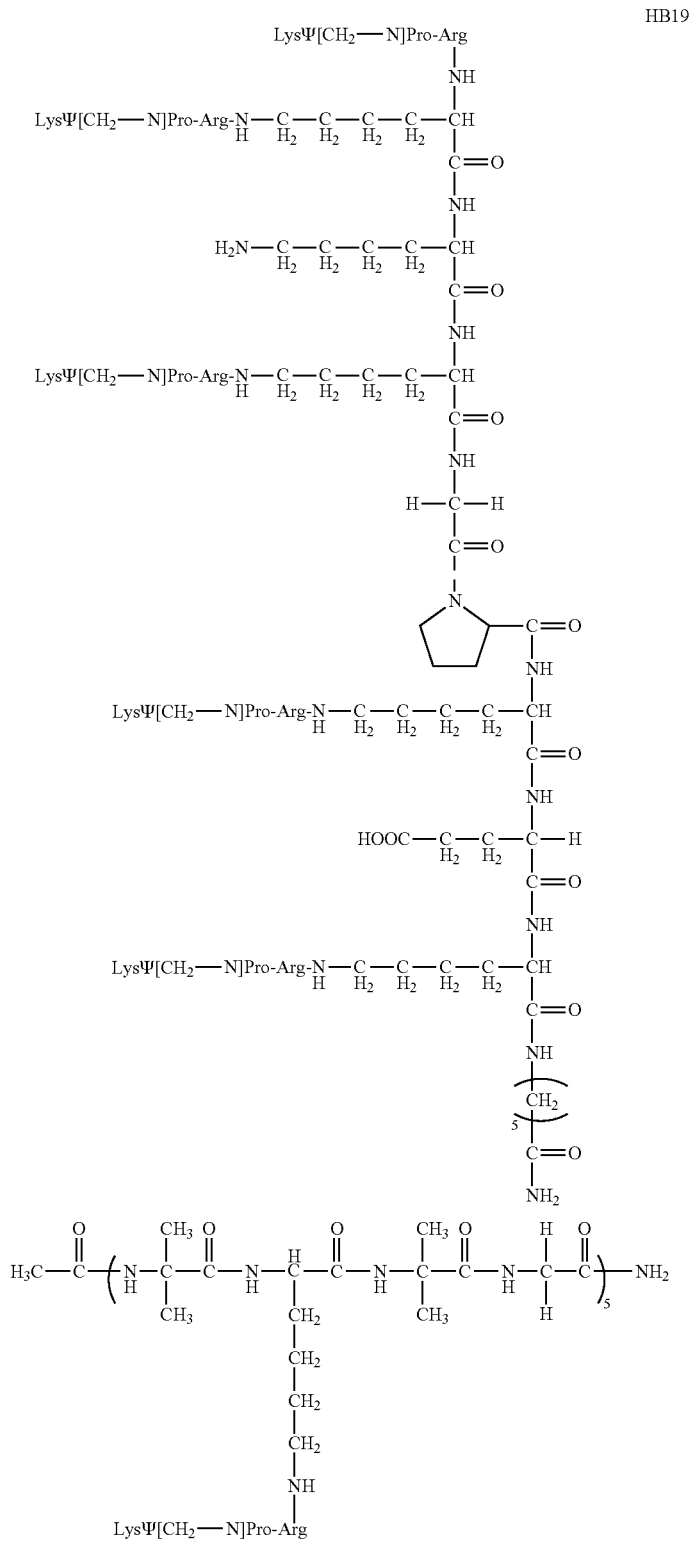
Nucant 2

-continued

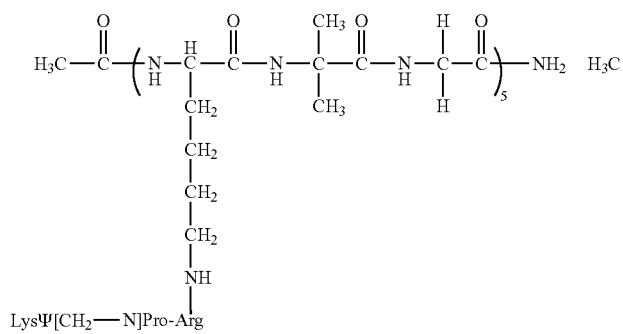

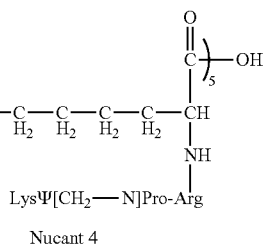

Nucant 4

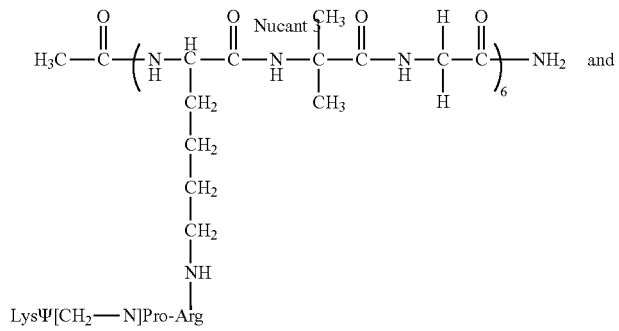

Nucant 6

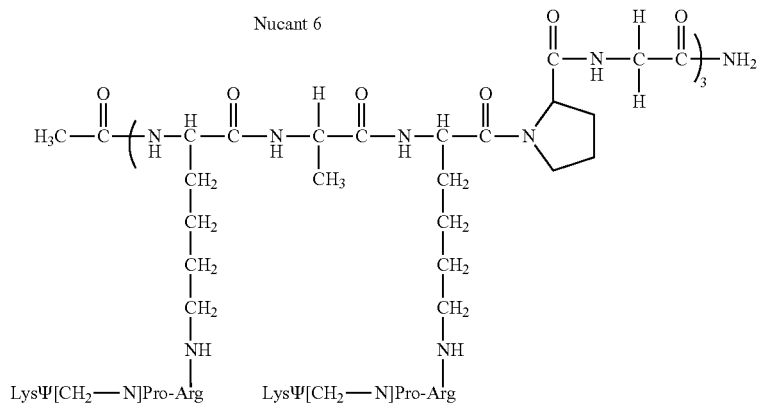

Nucant 7 wherein Lys residues in [(X)$_n$-Lys-Ψ-Pro-Arg-(X)$_m$] units of formula (I) are either all in L configuration or all in D configuration.

A preferred compound according to the invention is compound

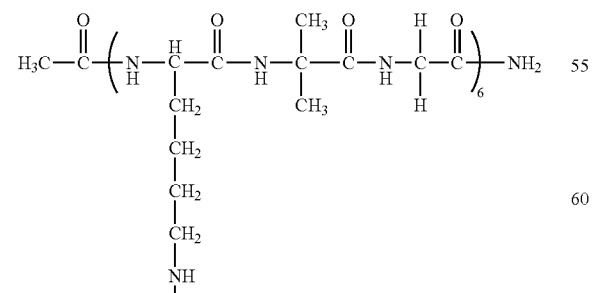

Nucant 6 wherein Lys residues in [(X)$_n$-Lys-Ψ-Pro-Arg-(X)$_m$] units of formula (I) are either all in L configuration or all in D configuration. A still more preferred compound is compound named Nucant 6L of formula:

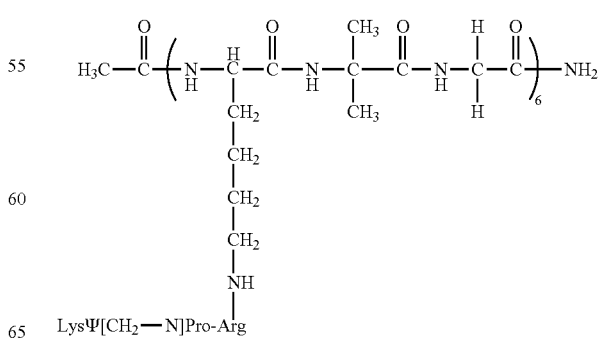

Nucant 6 wherein Lys residues in [(X)$_n$-Lys-Ψ-Pro-Arg-(X)$_m$] units of formula (I) are either all in L configuration.

As explained in introduction, a specific, non-conventional method must be used for preparing the KΨP dipeptide in order to be able to prepare the optically pure compounds according to the invention.

The synthesis of optically pure (L)Lys-Ψ-Pro or (D)Lys-Ψ-Pro dipeptides involves the preparation of a pure (L)Lys-Pro or (D)Lys-Pro dipeptide with a normal peptide amide bond, and then the reduction of the amide in amino using borate BH$_3$, as represented in following Scheme 1A and 1B and explained in more details in Example 1.

Scheme 1A: synthesis of optically pure (L)Lys-Ψ-Pro dipeptide

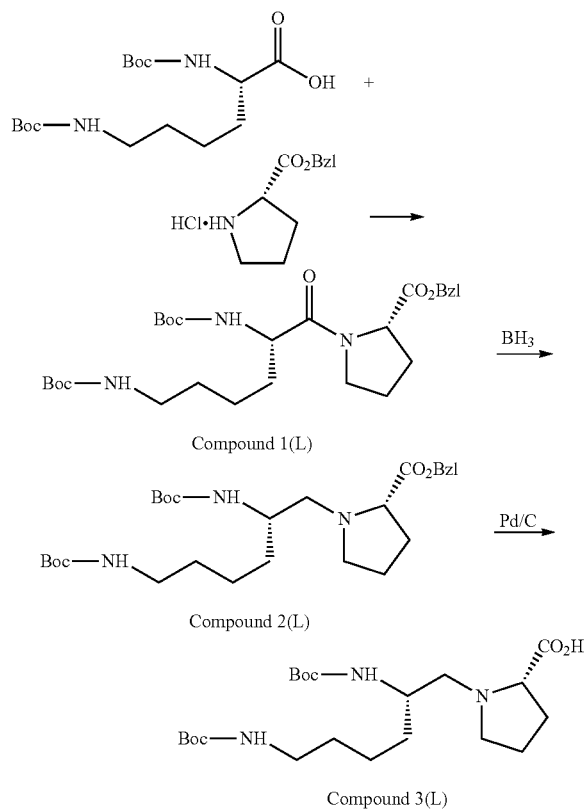

Scheme 1B: synthesis of optically pure (D)Lys-Ψ-Pro dipeptide

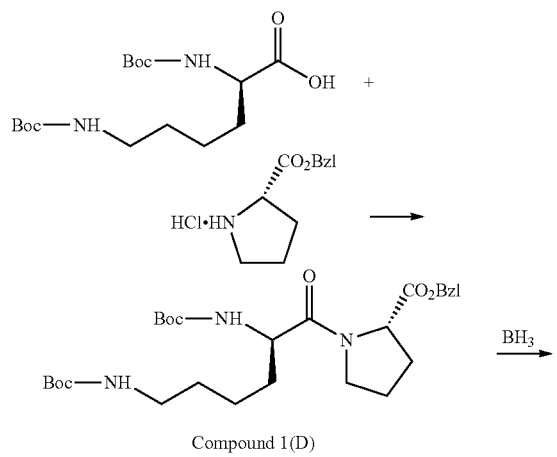

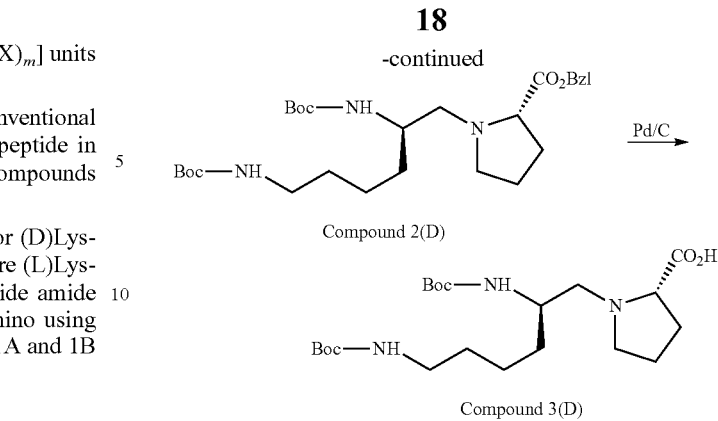

Chemical abbreviations used in the present application include:
Boc butoxycarbonyl
Bzl benzyl
DCHA Dicyclohexylamine
DCM dichloromethane
DIEA diisopropylethylamine,
DMF dimethylformamide
HOBt hydroxybenzotriazole
IPE diisopropyl ether
NMR Nuclear magnetic resonance
t-Bu tert-butyl
TLC Thin layer chromatography
THF tetrahydrofuran,
1-ethyl-3-[3-(N,N-dimethylamino)-propyl]carbodiimide-
WSCD Z benzyloxycarbonyl.

Once optically pure (L)Lys-Ψ-Pro or (D)Lys-Ψ-Pro dipeptides have been synthesized, they can be used for preparing a compound according to the invention in which Lys residues in [(X)$_n$-Lys-Ψ-Pro-Arg-(X)$_m$] units of formula (I) are either all in L configuration or all in D configuration.

In particular, when the support is a linear peptide with k lysine residues, the final optically pure compound according to the invention may be prepared using solid phase peptide synthesis and following the Fmoc/tBu methodology.

The invention thus also relates to a method for preparing a compound according to the invention in which the support is a linear peptide with k Lys residues, comprising:
a) preparing a dipeptide of formula (II) or (III)

L-Lys-Pro                                                    (II)

D-Lys-Pro                                                   (III)

b) reacting said dipeptide of formula (II) or (III) with borane BH$_3$ to obtain a dipeptide of formula (IV) or (V)

L-Lys-Ψ-Pro                                                 (IV)

D-Lys-Ψ-Pro                                                 (V)

c) providing a linear support peptide with k lysine residues linked to a solid phase,
d) coupling successively the (X)$_m$ residues, Arg residue, Lys-Ψ-Pro dipeptide, and (X)$_n$ residues to the support peptide by solid phase synthesis using the Fmoc/tBu methodology.

The more specific reaction conditions for implementing such a method are described in Example 1.3.

Such a method may be particularly implemented when the units do not include (X)$_m$ or (X)$_n$ residues, i.e. when n and m are 0 and the units are KΨPR units.

Said method may also be particularly used with preferred linear support peptides describes above, including peptides of sequences SEQ ID NO:1, SEQ ID NO:2, SEQ ID NO:3, or SEQ ID NO:4, and linear peptides with a helicoidal structure, including peptides comprising 3 to 8, preferably 5 or 6, units of sequence SEQ ID NO:6 or SEQ ID NO:7; and especially helicoidal linear support peptides constituted of a sequence selected from the group consisting of SEQ ID NO:8, SEQ ID NO:9, SEQ ID NO:10, SEQ ID NO:11, SEQ ID NO:12, and SEQ ID NO:13.

The invention further relates to a medicament comprising any compound according to the invention as described above, and to a pharmaceutical composition comprising any compound according to the invention as described above and a pharmaceutically acceptable carrier.

A "pharmaceutically acceptable" carrier or excipient means a carrier or excipient that does not cause any untoward effects in patients to whom it is administered. Such pharmaceutically acceptable carriers and excipients are well known in the art.

The pharmaceutical composition or medicament may also comprise additional compounds such as diluents, excipients, or even another active molecule that might be used in combination with the compounds according to the invention.

Said medicament of pharmaceutical composition may combine several of the compound(s) according to the invention. In particular, said medicament of pharmaceutical composition may in particular comprise one or more of the HB19, Nucant 2, Nucant 3, Nucant 4, Nucant 6, Nucant 7, Nucant 8 and Nucant 9 compounds described above, in which Lys residues in $[(X)_n\text{-Lys-}\Psi\text{-Pro-Arg-}(X)_m]$ pseudopeptide units of said compound of formula (I) are either all in L configuration or all in D configuration.

The medicament or pharmaceutical composition according to the invention may be used for the treatment of any disease in which the compounds according to the invention have some therapeutic effect.

In particular, the medicament or pharmaceutical composition according to the invention may be used for treating any disease involving deregulation of cell proliferation and/or angiogenesis.

The term "disease involving deregulation of cell proliferation and/or angiogenesis" means, in the context of the invention, any human or animal disease affecting one or more organs in which one or more abnormal cell proliferation phenomena are observed, as well as groups of cells or tissues and/or abnormal neovascularisation.

Evidently, such diseases include all types of cancer, such as adenoma, sarcoma, carcinoma, lymphoma, and especially cancer of the ovary, breast, pancreas, lymph node, skin, blood, lung, brain, kidney, liver, nasopharyngeal cavity, thyroid, central nervous system, prostate, colon, rectum, uterine, cervix, head and neck, testicles or bladder. They also include non-cancerous diseases of the skin such as epidermal or dermal cysts, psoriasis, angiomas, as well as ocular diseases such as age related macular degeneration (ARMD), diabetic retinopathy or neovascular glaucoma. Neurodegenerative diseases such as multiple sclerosis, Parkinson's and Alzheimer's or autoimmune diseases such as lupus, psoriasis, Crohn's disease or rheumatoid polyarthritis, as well as diseases related to atherosclerosis.

In a preferred embodiment, the medicament or pharmaceutical composition according to the invention may thus be used for treating cancer Indeed, the compounds according to the invention are demonstrated to have a very high efficiency for treating cancer (see Example 2). Examples of cancers that may be treated using the optically pure compounds according to the invention include all those described above.

In addition, previously described stereoisomer mixtures have been described to have anti-inflammatory properties, and the compounds according to the invention may also be used for treating an inflammatory disease. Thus, in another preferred embodiment, the medicament or pharmaceutical composition according to the invention may thus be used for treating inflammatory diseases.

The term <<inflammatory disease>> means any disease in which an inflammatory reaction has pathological consequences for the organism. In particular, inflammatory diseases in the context of the invention include autoimmune diseases (such as lupus or rheumatoid polyarthritis), septicaemia, septic shock, cardiac inflammatory diseases (carditis, and especially endocarditis, pericarditis, myocarditis, in particular those of an infectious origin such as those caused by *Staphylococcus aureus*), graft rejection, trauma, inflammatory diseases of the joints (notably, different forms of arthritis), inflammatory diseases of the gastrointestinal system (notably, colitis, enteritis, gastritis, gastroenteritis, and chronic inflammatory diseases of the intestine such as Crohn's disease and haemorrhagic rectocolitis (HRC)), inflammatory diseases of the skin (eczema, allergic contact dermatitis, psoriasis, dermatosis), inflammatory diseases of the respiratory system, especially chronic obstructive pulmonary disease (COPD), and allergies.

In an advantageous embodiment, the inflammatory disease is an autoimmune disease, in particular lupus or rheumatoid arthritis. In another advantageous embodiment, the inflammatory disease is septic shock. In yet another advantageous embodiment, the inflammatory disease is an endocarditis, particularly endocarditis of infectious origin, such as that caused by *Staphylococcus aureus*.

The medicament or pharmaceutical composition according to the invention may also be used for improving wound healing.

Typical wounds envisaged in the present invention are both open and closed wounds, including chronic wounds like chronic leg ulcers, diabetic ulcers, pressure sores, acute wounds (such as grazes, knife cuts), that would benefit from wound healing promotion, wounds which are difficult to heal such as, but not limited to infected wounds, necrotic wounds, burn wounds (of different degrees) including sunburn, post-operative wounds, skin transplants and traumatic wounds.

In particular, they may be used for improving cicatrisation of skin wounds.

Medicaments or pharmaceutical composition according to the invention may be administered by any suitable administration route, including but not limited to orally, subcutaneously, intravenously, intracerebrally, intranasally, topically, transdermally, intraperitoneally, intramuscularly, intrapulmonary, vaginally, rectally, intraocularly, or in any other acceptable manner The invention also relates to a method for treating a disease involving deregulation of cell proliferation and/or angiogenesis in a subject in need thereof, comprising the administration of a therapeutically efficient amount of a compound according to the invention as described above.

In a preferred embodiment, the invention relates to a method for treating cancer in a subject in need thereof, comprising the administration of a therapeutically efficient amount of a compound according to the invention as described above.

In another preferred embodiment, the invention further concerns a method for treating any inflammatory disease described above in a subject in need thereof, comprising the administration of a therapeutically efficient amount of a compound according to the invention as described above.

The invention is also directed to a method for improving wound healing in a subject in need thereof, comprising the administration of a therapeutically efficient amount of a compound according to the invention as described above.

The invention is further illustrated by the following figures and experimental examples. These data are provided for illustrative purpose only and should not be construed as limiting the scope of the invention.

EXAMPLES

Example 1

Figure 1:
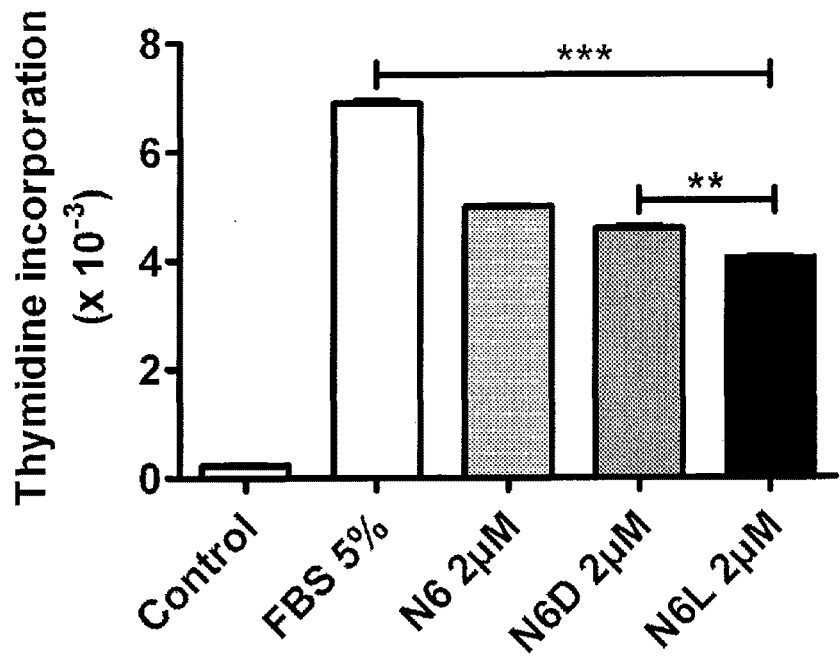
FIG. 1: Activity of NucAnts 6, 6D and 6L on the $^3$H-thymidine incorporation in NIH 3T3 cells. NIH-3T3 cells ($2\times10^5$) were seeded in 48-multiwell plates and incubated 24 hours for adhesion. The cells were serum starved 24 hours before being stimulated with 5% FBS with or not the peptides for 18 hours. Then, 1 µCi of [$^3$H]-thymidine was added in each well and the incubation was prolonged for 6 hours. The wells were washed with PBS, and DNA was precipitated with ice-cold 10% trichloroacetic acid. The cells were then lysed in 0.2N NaOH, and the [$^3$H]-thymidine incorporated was measured in a scintillation counter. All experiments were performed in triplicate. Bars, ±sem (n=3), *$p<0.05$, $p<0.01$, *$p<0.001$, statistically significant compared with control (Student's t test).

Synthesis of Nucant 6 Compounds with Either all Lys Residues in Formula (I) in L Configuration or all Lys Residues in Formula (I) in D Configuration

1.1. Definition of Compounds Nucant 6, Nucant 6L and Nucant 6D

Nucant 6 represents a pseudopeptide with a linear support peptide of sequence Ac-Lys-Aib-Gly-Lys-Aib-Gly-Lys-Aib-Gly-Lys-Aib-Gly-Lys-Aib-Gly-Lys-Aib-Gly-CONH$_2$ (SEQ ID NO: 13), to which 6 KΨPR units are coupled on the lateral chain of the 6 lysine residues of the linear support peptide. It displays the following formula:

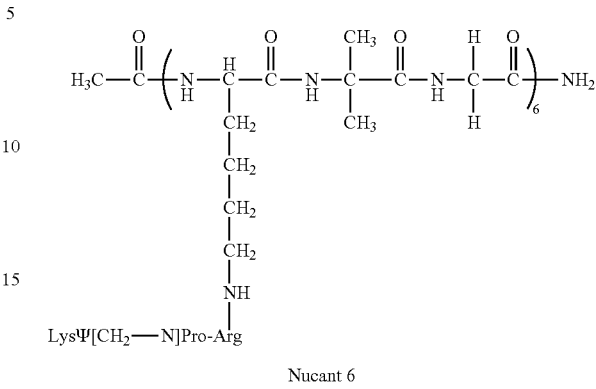

Nucant 6 in which the lysine residue of each KΨPR unit may be either in a L or D configuration.

As explained in general description, the usual method for preparing a KΨP unit, which is based on a reductive amination of Boc-Lys(Boc)-CHO (aldehyde) and proline (with an amino group), results in an epimerization of the lysine residue. The resulting KΨP units are thus an useparable mixture of (L)KΨP and (D)KΨP dipeptide units. Using such a mixture for coupling these KΨP units to a support would result in a pseudopeptide in which the various KΨP units may each be in either L or D configuration. A mixture of diastereoisomers of the pseudopeptide would be obtained.

In the following, Nucant 6 corresponds to such a mixture of diastereoisomers.

In contrast, Nucant 6L refers to a pseudopeptide with the above formula, in which all lysine residues in KΨP units are in L configuration, while Nucant 6D refers to a pseudopeptide with the above formula, in which all lysine residues in KΨP units are in D configuration.

1.2. Synthesis of a Mixture of Diasteroisomers of K-Ψ-P Units

Using the conventional method (see references 2 and 3), a Mtt protected linear support peptide of formula Ac-Lys(Mtt)-Aib-Gly-Lys(Mtt)-Aib-Gly-Lys(Mtt)-Aib-Gly-Lys(Mtt)-Aib-Gly-Lys(Mtt)-Aib-Gly-Lys(Mtt)-Aib-Gly-Rink amide MBHA resin was first prepared.

The Mtt-<<protecting group was then cleaved with a mixture of dichloromethane (DMC)-triisopropylsilane-trifluoroacetic acid (TFA) (93:5:2, by volume) (five times, 5 min each) and the resin was washed several times with DCM and DMF. Fmoc-Lys(Mtt)-OH coupling and Mtt deprotection were repeated again three times as described above. The N$^\alpha$-Fmoc protecting groups were then removed with 25% piperidine in DMF. The free amino functions were subsequently acylated with a 15-fold excess of Fmoc-Arg(Pbf)-OH and Fmoc-Pro-OH The reduced amide bond between Lys and Pro was then formed on a resin by reductive amination of the N-protected aminoaldehyde Boc-Lys(Boc)-CHO (2.5-fold excess, twice) with Proline in dimethylformamide containing 1% acetic acid along 1 h 10).

1.3. Synthesis of Pure (L)K-Ψ-P Units

The synthesis of (L)K-Ψ-P units, in which all lysine residues are in L configuration, has been performed as described in Scheme 1A (see page 17).

More precisely, the following protocol was used:

Step 1: Synthesis of Boc-L-Lys(Boc)-Pro-OBzl (Compound 1)

Boc-L-Lys(Boc)-OH.DCHA (75 g, 0.142 mole) is dissolved in a mixture of AcOEt (375 ml) and KHSO4 (1M)(375 ml). The organic phase is washed with KHSO4 (1M)(200 ml), water (200 ml) and NaCl sat. (100 ml). The resulting product is dried on Na2SO4 and concentrated to dryness.

The residue is dissolved in DMF (200 ml). HCl.H-Pro-OBzl (32.6 g, 0.135 mole), HOBt.H2O (23.9 g, 0.156 mole) and DIEA (23.2 ml, 0.135 mole) are added. Medium is cooled to 0-5° C. WSCD (32.7 g, 0.171 mole) is introduced by portions and the reaction mixture is stirred at room temperature during 3 h.

The mixture is poured onto NaHCO3 (5%) (2 L). The product is extracted with AcOEt (750 ml). The organic phase is washed with 3×NaHCO3 (5%) (300 mL), 2×K2CO3 (5%) (300 ml), 2×KHSO4 (1M)(300 ml) and NaCl sat. (200 ml). The resulting product is dried on Na2SO4 and concentrated to dryness. The residue is coevaporated twice with cyclohexane (200 ml). 78 g of oil are obtained. Yield>100%. HPLC: 96.9%. MS ES+533.9 (M+1).

Step 2 Synthesis of Boc-L-Lys(Boc)-Ψ(CH$_2$—N)-Pro-OBzl (Compound 2)

Boc-L-Lys(Boc)-Pro-OBzl (33.4 g, 62.6 mmole) is dissolved in anhydrous THF (50 ml) and cooled to C. A solution of BH3/THF (1M) (125 ml, 125 mmole) is added dropwise during 30 min while maintaining temperature at 0-4° C. It is incubated during 30 min at 0-4° C. then at 20° C. during 21 h. HPLC control (40-100%): 39.3%

The medium is cooled to 0° C. A solution of KHSO4 (1M) (300 ml) is added while maintaining temperature at <10° C. then the medium is stirred at 20° C. during 1 h. It is then concentrated to remove THF. The medium is neutralized by a solution of K2CO3 (83 g/100 ml water) to reach pH 9.8.

The product is extracted with 450 ml of DCM, dried on Na2SO4 and concentrated to dryness (28.1 g). The crude product is purified on a silica column (800 g) using AcOEt/cyclohexane (4/6) as eluant. Suitable fractions are collected and concentrated to dryness. 11.8 g of oil are obtained (Yield 37%).

Analysis: HPLC 68.2% and 29.9% of benzylic alcohol (s/s). Estimated 92% pure (p/p).

Step 3 Synthesis of Boc-L-Lys(Boc)-Ψ(CH2-N)-Pro-OH (Compound 3)

Compound 2 (11.8 g, 22.7 mmole, estimated at 92% p/p) in dissolved in ethanol (120 ml).

Pd/C (50% of water) (600 mg) is added. Void-nitrogen is degassed twice and the mixture is hydrogenated under hydrogen overnight.

TLC Control: AcOEt/Cyclohexane (5/5)

The catalyst is eliminated by filtration and the filtrate is concentrated to dryness. IPE (100 ml) is added.

The precipitate is filtrated and washed twice with IPE (50 ml). 9.2 g of solid are obtained (Yield 94%). HPLC analysis 87%.

The crude product is dissolved in DCM (50 ml). Insolubles are filtrated and IPE is added to the filtrate in order to precipitate the product 4.5 g are obtained from the 1$^{st}$ C: HPLC 99.3%; MS ES+430.1 (M+1). The remaining solution is precipitated with cyclohexane and IPE. 2.4 g are obtained from this second V (HPLC 75.4%). Global yield: 70.7%.

Results

Two hydrogenation experiments were performed. Results are summarized in following Table 1:

|  | Composé 2 | Composé 3 | HPLC |
|---|---|---|---|
| FC25130 | 17 g<br>Estimé à 91% p/p | 8.43 g<br>Rdt 61% | 95% |
| FC25152 | 11.8 g<br>Estimé à 92% p/p | 4.5 g Rdt 46.2%<br>2.9 g Rdt 30%<br>Rdt global 76.2% | 99.6%<br>75.4% |

Due to the low absorbance of compound 3 in UV (210 nm), compound 3 can be obtained with a HPLC purity of >95%.

1.4. Synthesis of Pure (D)K-Ψ-P Units

Boc-D-Lys(Boc)-Ψ(CH2-N)-Pro-OH is prepared using the same protocol as above, except that Boc-D-Lys(Boc)-OH.DCHA is used instead of Boc-L-Lys(Boc)-OH.DCHA, as displayed on Scheme 1B (see page 17).

27.7 g of Boc-D-Lys(Boc)-Ψ(CH2-N)-Pro-OH are obtained from 100 g of Boc-D-Lys(Boc)-OH.DCHA. Global yield is 36%. Due to the low absorbance of compound 3 in UV (210 nm) and to the difficulty to precipitate (D) deriviative, we were not able to obtain the product with HPLC purity >95%. The product quality is estimated using TLC and NMR 1H. The amount of benzylic alcohol is estimated to 2% by NMR 1H.

1.5. Distinction of the Two (L) and (D) Derivatives

Co-injection in HPLC of the two compounds 3 (L et D) results in a clear separation of the two diastereoisomers.

1.6. Synthesis of Nucant 6, Nucant 6L, and Nucant 6L

Introduction

The three pseudopeptides were synthesized using solid phase synthesis and following the Fmoc/tBu methodology, using either a mixture of diastereoisomers of KΨP units (see §1.2), pure (L)KΨP units (see §1.3), or pure (D)KΨP units (see §1.4). The coupling of amino acids was performed step by step onto Rink amide PS resin. After removal of the Mtt groups of lysine, Arg and Lys-Ψ(CH2N-Pro) were coupled onto the side chain of the six lysines of the linear support peptide. The cleavage was carried out in TFA/H2O. The crude peptide was purified by RP-HPLC to give the pure peptide.

Preparation of a Mtt Protected Linear Support Peptide

Ac-Lys(Mtt)-Aib-Gly-Lys(Mtt)-Aib-Gly-Lys(Mtt)-Aib-Gly-Lys(Mtt)-Aib-Gly-Lys(Mtt)-Aib-Gly-Lys(Mtt)-Aib-Gly-Rink amide MBHA resin.

The linear peptide was assembled on 1 mmole of Rink amide MBHA resin (0.33 mequi/g) as solid support. The coupling of Fmoc-amino acid and deprotection are described below:

2 eq of Fmoc-Amino acid, 2 eq of coupling reagent were dissolved in DMF (2-3 mL per mmole of amino acid). The solution was poured into the reaction mixture containing the resin and 4-5 eq of DIEA were added.

TABLE 2 reaction conditions

| Step | Solvent | Time | cycle |
|------|---------|------|-------|
| 1 | Coupling/DMF | (*)min | Coupling |
| 2 | DMF | 3 × 1 min | washing |
| 3 | Piperidine/DMF (25%) | 1 min(**) | Deprotection |
| 4 | Piperidine/DMF (25%) | 2 × 15 min | Deprotection |
| 5 | DMF | 7 × 1 min(**) | Washing |

(*)Completion of coupling was determined by the Kaiser test.
(**)The solvent volume for washing and deprotection was 10 mL/gram of peptide-resin.

For the assembling the following conditions were (Table 3):

|  | Amino acid | PyBOP/HOBt | HATU | DIEA |
|--|------------|------------|------|------|
| Fmoc-Gly-OH | 3 eq | 3 eq/3 eq | — | 7.5 eq |
| Fmoc-Aib-OH | 2 eq | 2 eq/2 eq | — | 5 eq |
| Fmoc-Lys(Mtt)-OH | 2 eq | — | 2 eq | 4 eq |

Deprotection of Mtt

Linear Peptide

Ac-Lys-Aib-Gly-Lys-Aib-Gly-Lys-Aib-Gly-Lys-Aib-Gly-Lys-Aib-Gly-Lys-Aib-Gly-Rink amide MBHA resin Six Mtt groups were removed using 20% de hexafluoroisopropanol/DCM for 2 hours (10 ml/g of resin).

Final Synthesis of Nucant 6L

Coupling of Amino Acids to Side Chain

TABLE 4

Reaction conditions for coupling of amino acids to side chains

|  | Amino acid | PyBOP/HOBt | DIC/HOBt | DIEA |
|--|------------|------------|----------|------|
| Fmoc-Arg(Pbf)-OH | 12 eq | 12 eq/12 eq | — | 60 eq |
| Boc-Lys(Boc)-Ψ(CH2N-Pro)-OH | 9 eq | — | 9 eq/9 eq | — |

Fmoc-Arg(Pbf)-OH and Boc-Lys(Boc)-Ψ(CH2N-Pro)-OH were coupled onto the side chain of Lysine using a 2 eq of amino acid, HATU and DIEA.

Cleavage

The cleavage of protected peptide from the resin was performed using TFA/H2O (95/5) and yielded 4.67 g of crude product.

Purification

The crude product (4.67 g) was purified by RP-HPLC using water/acetonitrile containing 0.1% TFA as eluents. The fractions with a purity >95% were collected and freeze dried to give 657 mg of powder as TFA salt. Yield of purification: 14.1%. The TFA salt was exchanged with AcOH using Dowex 1×2 to afford 524 mg of powder (net peptide content: 76.7%).

Final Synthesis of Nucant 6 and Nucant 6D

The final synthesis of Nucant 6 and Nucant 6D was performed using a similar procedure.

For Nucant 6D, 293 mg of AcOH salt was obtained (net peptide content: 77.2%) from 1 mmole of resin. Global yield 5.9%.

Example 2

Effect of Compounds Nucant 6, Nucant 6L and Nucant 6D on the Growth of Tumor Cells In Vitro 2.1. Materials and Methods Compounds Used Compounds defined as Nucant 6, Nucant 6L and Nucant 6D in Example 1 were used.

Test of the Inhibitory Activity on the In Vitro Proliferation of NIH 3T3 Cells

NIH-3T3 cells ($2 \times 10^5$) were seeded in 48-multiwell plates and incubated 24 hours for adhesion. The cells were serum starved 24 hours before being stimulated with 5% FBS with or not the peptides for 18 hours. Then, 1 μCi of [$^3$H]-thymidine was added in each well and the incubation was prolonged for 6 hours. The wells were washed with PBS, and DNA was precipitated with ice-cold 10% trichloroacetic acid. The cells were then lysed in 0.2N NaOH, and the [$^3$H]-thymidine incorporated was measured in a scintillation counter.

Test of the Inhibitory Activity on the In Vitro Proliferation of MDA-MB 435 Cells MDA-MB 435 cells ($2 \times 10^4$) were seeded in 24-multiwell plates and incubated for 24 hours for adhesion. Cells were treated everyday for 3 days with medium removing. At the fifth day, the cells were counted by crystal violet staining. So, they were washed twice with PBS and fixed for 5 minutes with absolute ethanol. Then, the cells were stained with a 0.2% crystal violet, 2% ethanol solution for 15 minutes, washed twice with distillated water and dried at room temperature for 45 minutes. Then the crystal violet was solubilized with 500 μl of SDS 1%. The absorbance at 595 nm was evaluated with 100 μl of each sample using a microplate reader.

Test of the Inhibitory Activity on the In Vitro Proliferation of T29 Cells

T29 cells were plated (5000 cells per well) in 24 wells plate. Cells were treated with the peptides once and leaved for 3 days at 37° C., 5% CO2. Then, cells were stained with Trypan blue and counted at the Mallassez cell.

2.2. Results

Figure 2:
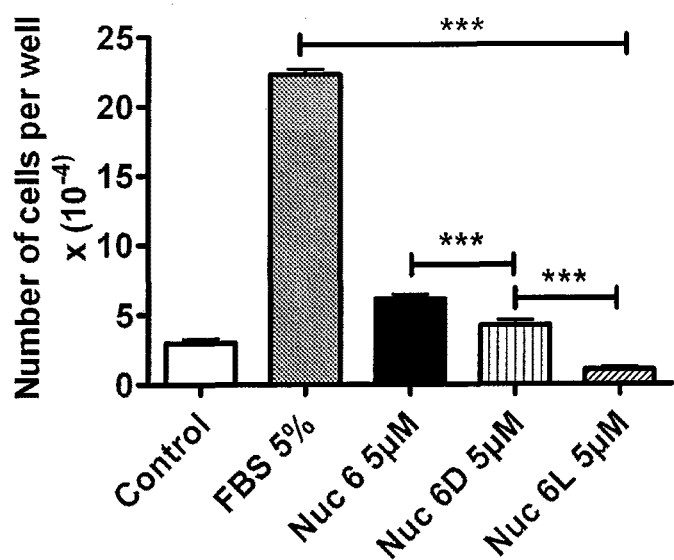
FIG. 2: NucAnts 6, 6D and 6L activities on MDA-MB 435 proliferation. Cells ($2\times10^4$) were seeded in 24-multiwell plates and incubated for 24 hours for adhesion. Cells were treated everyday for 3 days with medium removing. At the fifth day, the cells were counted by crystal violet staining. So, they were washed twice with PBS and fixed for 5 minutes with absolute ethanol. Then, the cells were stained with a 0.2% crystal violet, 2% ethanol solution for 15 minutes, washed twice with distillated water and dried at room temperature for 45 minutes. Then the crystal violet was solubilized with 500 µl of SDS 1%. The absorbance at 595 nm was evaluated with 100 µl of each sample using a microplate reader.
Figure 3:
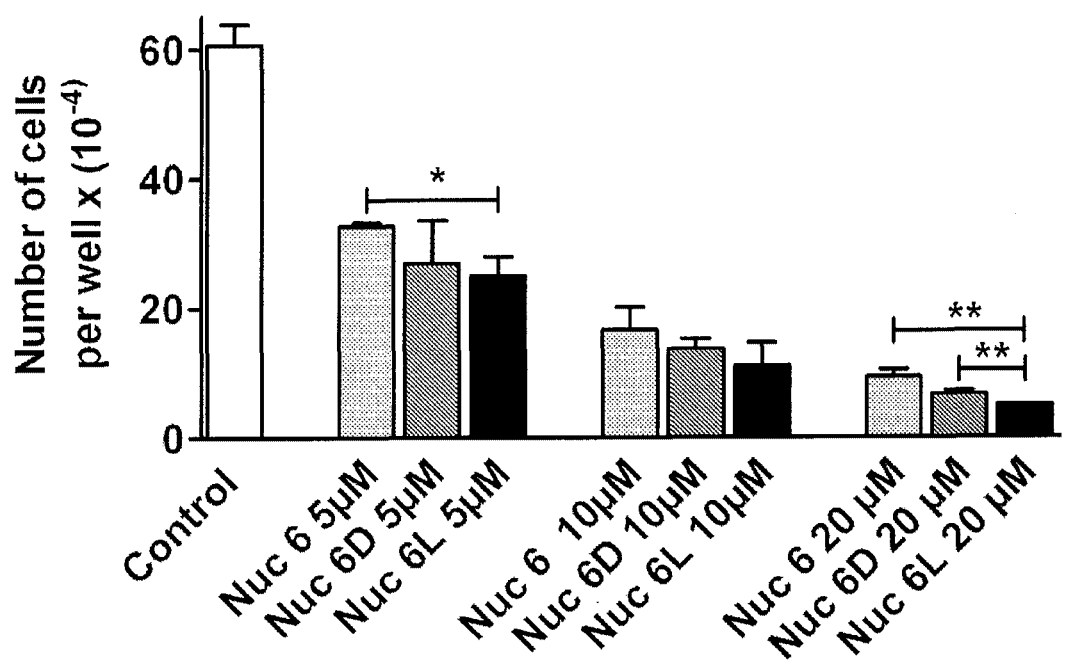
FIG. 3: NucAnts 6, 6D and 6L activities on T29 proliferation. T29 cells were plated (5000 cells per well) in 24 wells plate. Cells were treated with the peptides once and leaved for 3 days at 37° C., 5% CO2. Then, cells were stained with Trypan blue and counted at the Mallassez cell. Bars, ±sem (n=3), *$p<0.05$, $p<0.01$, *$p<0.001$, statistically significant compared with control (Student's t test).

The various Nucant 6 compounds (complex undefined and non separable mixture obtained using the conventional synthesis method, L, D) have been tested for their inhibitory activity on the cellular proliferation of NIH 3T3 (FIG. 1), MDA-MB 435 (FIG. 2) or T29 cells (FIG. 3).

For NIH 3T3 (FIG. 1), MDA-MB 435 (FIG. 2) and T29 (FIG. 3) cells, results show that compounds Nucant 6L and Nucant 6D have an increased inhibitory activity on cellular proliferation compared to compound Nucant 6 (complex undefined and non separable mixture obtained using the conventional synthesis method).

These results clearly demonstrate that optically pure compounds, with the Lysine residues in [$(X)_n$-Lys-Ψ-Pro-Arg-$(X)_m$] pseudopeptide units either all in L configuration or all in D configuration have an increased anti-proliferative activity compared to the non optically pure Nucant 6 compound.

2.3. Conclusion

The above results clearly show that compound Nucant 6L or D according to the invention has an increased anti-proliferative capacity compared to the Nucant 6 compound constituted of a complex undefined and non separable mixture of stereoisomers that was systematically obtained using the conventional synthesis method.

REFERENCES

1. WO2007/125210
2. US20040002457A1
3. Nisole S. et al. "The HB-19 pseudopeptide 5[Kpsi (CH2N) PR]-TASP inhibits attachment of T lymophocyte- and macrophage-tropic HIV to permissive cells." AIDS Res Hum Retroviruses. 2000 Feb. 10; 16(3):237-49.
4. M. Cushman, Y-i. Oh, T. D. Copeland, S. W. Snyder, and Stephen Oroszlan, "Development of Methodology for the Synthesis of Stereochemically Pure PheΨ[CH2N] Pro Linkages in HIV Protease Inhibitors," J. Org. Chem. 56, 4161 (1991).

---

The invention claimed is:

1. A compound comprising at least 3 optically pure pseudopeptides coupled to a support as in formula (I):

$$[(X)_n\text{-Lys-}\Psi\text{-Pro-Arg-}(X)_m] \quad (I)$$

Wherein
   each X independently represents any amino acid;
   n is 0 or 1;
   m is an integer between 0 and 3;
   Ψ is a reduced bond of formula (—CH2N—) replacing the peptide amide bond between Lys and Pro; and
   wherein Lys residues in $[(X)_n\text{-Lys-}\Psi\text{-Pro-Arg-}(X)_m]$ pseudopeptide units of said compound of formula (I) are either all in L configuration or all in D configuration.

2. The compound according to claim 1, wherein n is 0 and m is 0.

3. The compound according to claim 1, consisting of between 3 and 8 pseudopeptide units.

4. The compound according to claim 1, consisting of 5 or 6 pseudopeptide units.

5. The compound according to claim 1, wherein said support is a linear peptide comprising at least 3 Lys residues.

6. The compound according to claim 5, wherein said linear support peptide has a sequence selected from the group consisting of Lys-Lys-Lys-Gly-Pro-Lys-Glu-Lys-Gly-Cys (SEQ ID NO: 1), Lys-Lys-Lys-Lys-Gly-Cys (SEQ ID NO: 2), Lys-Lys-Lys-Lys-Gly-Pro-Lys-Lys-Lys-Lys-Gly-Ala (SEQ ID NO: 3), Lys-Lys-Gly-Pro-Lys-Glu-Lys-AhxCONH₂ (SEQ ID NO: 4), and Ac-Lys-Ala-Lys-Pro-Gly-Lys-Ala-Lys-Pro-Gly-Lys-Ala-Lys-Pro-Gly-CONH₂ (SEQ ID NO: 5).

7. The compound according to claim 5, wherein said linear support peptide displays a helicoidal structure.

8. The compound according to claim 7, wherein said helicoidal linear support peptide comprises at least 3, preferably 3 to 8, preferably 5 or 6, units of sequence Aib-Lys-Aib-Gly (SEQ ID NO: 6) or Lys-Aib-Gly (SEQ ID NO: 7).

9. The compound compound according to claim 8, wherein said helicoidal linear support peptide is constituted of a sequence selected from the group consisting of Aib-Lys-Aib-Gly-Aib-Lys-Aib-Gly-Aib-Lys-Aib-Gly-Aib-Lys-Gly-Aib-Lys-Aib-Gly-Aib-Lys-Aib-Gly (SEQ ID NO: 8), Lys-Aib-Gly-Lys-Aib-Gly-Lys-Aib-Gly-Lys-Aib-Gy-ys-Aib-Gly-Lys-Lys-Aib-Gly (SEQ ID) NO: 9), Ac-Aib-Lys-Aib-Gly-Aib-Lys-Aib-Gly-Aib-Lys-Aib-Gly-Aib-Lys-Aib-Gly-Aib-Lys-Aib-Gly-CONH2 (SEQ ID NO: 10), Ac-Lys-Aib-Gly-Lys-Aib-Gly-Lys-Aib-Gly-Lys-Aib-Gly-Lys-Aib-Gly-CONH2 (SEQ ID NO: 11), Ac-Aib-Lys-Aib-Gly-Aib-Lys-Aib-Gly-Aib-Lys-Aib-Gly-Aib-Lys-Aib-Gly-Aib-Lys-Aib-Gly-Aib-Lys-Aib-Gly-CONH2 (SEQ ID NO: 12), or Ac-Lys-Aib-Gly-Lys-Aib-Gly-Lys-Aib-Gly-Lys-Aib-Gly-Lys-Aib-Gly-Lys-Aib-Gly-CONH2 (SEQ ID NO: 13).

10. The optically pure compound according to claim 1, selected from the group consisting of:

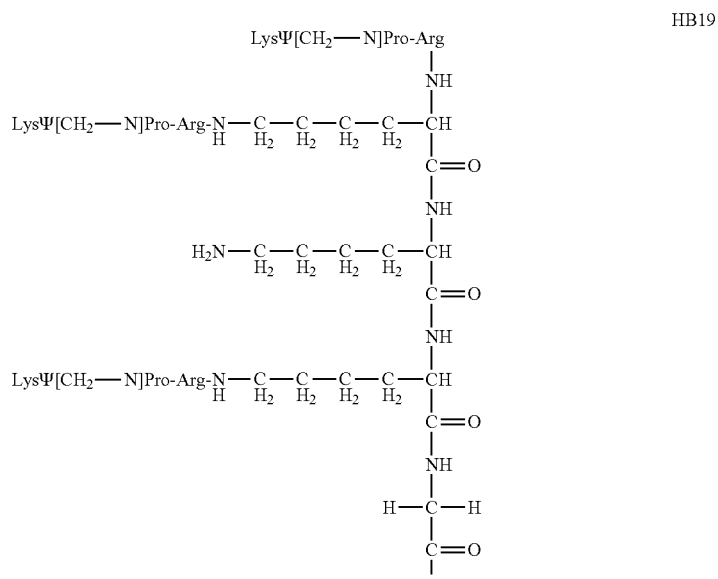
HB19
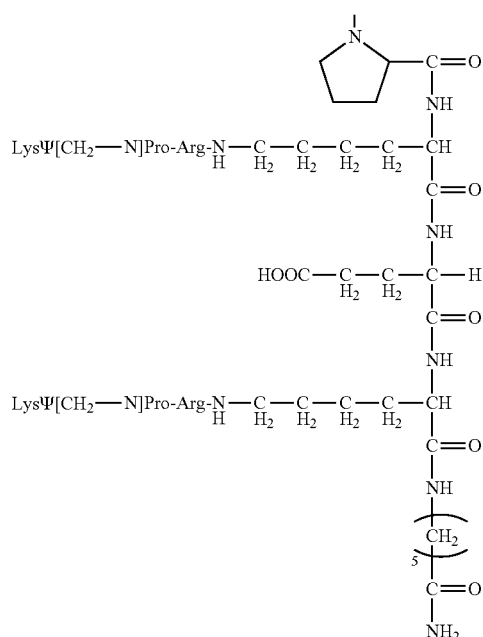
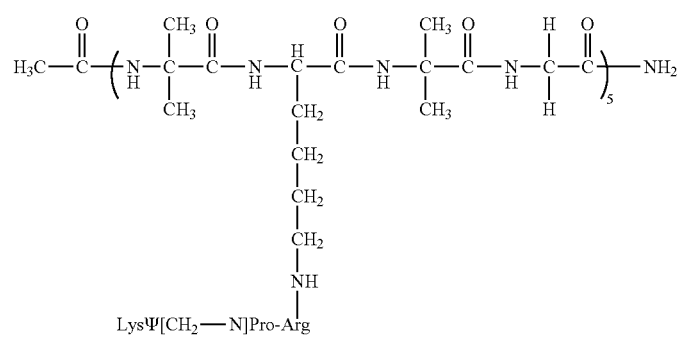
Nucant 2

-continued
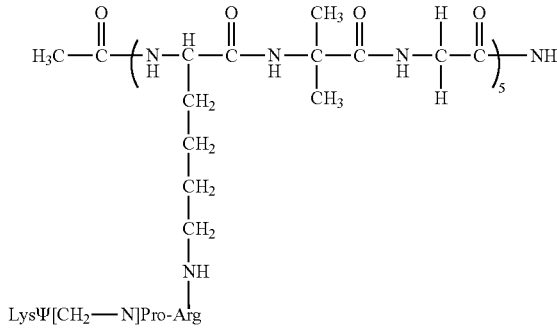
Nucant 3
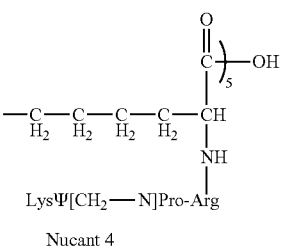
Nucant 4
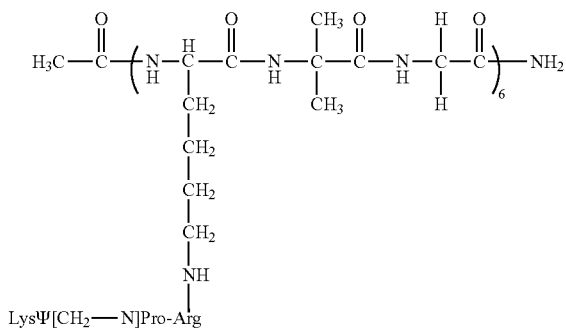
Nucant 6
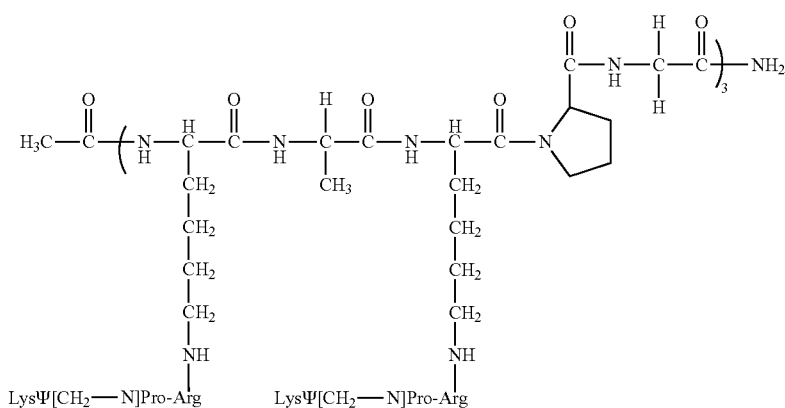
Nucant 7
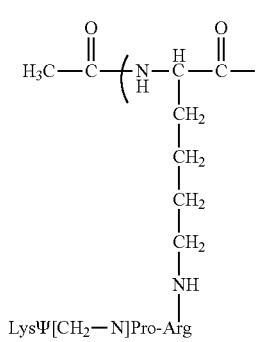
Nucant 8
and
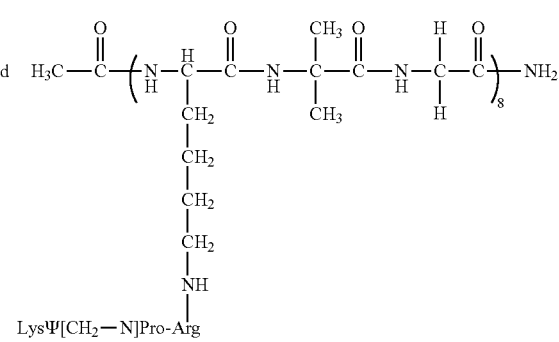
Nucant 9 wherein Lys residues in [(X)$_n$-Lys-Ψ-Pro-Arg-(X)$_m$] units of formula (I) are either all in L configuration or all in D configuration.

11. A method for preparing a compound according to claim 5, comprising:
   a) preparing a dipeptide of formula (II) or (III)

L-Lys-Pro                                    (II)

D-Lys-Pro                                   (III)

b) reacting said dipeptide of formula (II) or (III) with borate BH3 to obtain a dipeptide of formula (IV) or (V)

L-Lys-Ψ-Pro                              (IV)

D-Lys-Ψ-Pro                            (V)

c) providing a linear support peptide comprising at least k lysine residues linked to a solid phase,
   d) coupling successively the (X)$_m$ residues, Arg residue, Lys-Ψ-Pro dipeptide, and (X)$_n$ residues to the support peptide by solid phase synthesis using the Fmoc/tBu methodology.

12. A pharmaceutical composition comprising a compound according to claim 1 and a pharmaceutically acceptable carrier.

13. A method for treating cancer or inflammatory diseases in a subject in need thereof, comprising the administration of a therapeutically efficient amount of a compound according to claim 1.

14. A method for improving wound healing in a subject in need thereof, comprising the administration of a therapeutical iv efficient amount of a compound according to claim 1.

15. The compound according to claim 1, wherein n is 0, m is 0, consisting of between 3 and 8, and said support is a linear peptide comprising at least 3 Lys residues.

16. The compound according to claim 15, wherein k said support is selected from the group consisting of Lys-Lys-Lys-Gly-Pro-Lys-Glu-Lys-Gly-Cys (SEQ ID NO: 1), Lys-Lys-Lys-Lys-Gly-Cys (SEQ ID NO: 2), Lys-Lys-Lys-Lys-Gly-Pro-Lys-Lys-Lys-Lys-Gly-Ala (SEQ ID NO: 3), Lys-Lys-Gly-Pro-Lys-Glu-Lys-AhxCONH$_2$ (SEQ ID NO: 4), Ac-Lys-Ala-Lys-Pro-Gly-Lys-Ala-Lys-Pro-Gly-Lys-Ala-Lys-Pro-Gly-CONH$_2$ (SEQ ID NO: 5), Aib-Lys-Aib-Gly-Lys-Aib-Gly-Aib-Lys-Aib-Gly-Aib-Lys-Aib-Gly-Aib-Lys-Aib-Gly-Aib-Lys-Aib-Gly (SEQ ID NO: 8), Lys-Aib-Gly-Lys-Aib-Gly-Lys-Aib-Gly-Lys-Aib-Gly-Lys-Aib-Gly (SEQ ID NO: 9), Ac-Aib-Lys-Aib-Gly-Aib-Lys-Aib-Gly-Aib-Lys-Aib-Gly-Aib-Lys-Aib-Gly-Aib-Lys-Aib-Gly-CONH$_2$ (SEQ ID NO: 10), Ac-Lys-Aib-Gly-Lys-Aib-Gly-Lys-Aib-Gly-Lys-Aib-Gly-Lys-Aib-Gly-Lys-Aib-Gly-CONH2 (SEQ ID NO: 11), Ac-Aib-Lys-Aib-Gly-Aib-Lys-Aib-Gly-Aib-Lys-Aib-Gly-Aib-Lys-Aib-Gly-Aib-Lys-Aib-Gly-Aib-Lys-Aib-Gly-CONH$_2$ (SEQ ID NO: 12), and Ac-Lys-Aib-Gly-Lys-Aib-Gly-Lys-Aib-Gly-Lys-Aib-Gly-Lys-Aib-Gly-Lys-Aib-Gly-CONH$_2$ (SEQ ID NO: 13).

17. A pharmaceutical composition comprising a compound according to claim 10 and a pharmaceutically acceptable carrier.

18. A method for treating cancer or inflammatory diseases in a subject in need thereof comprising the administration of a therapeutically efficient amount of a compound according to claim 10.

19. A method for improving wound healing in a subject in need thereof, comprising the administration of a therapeutically efficient amount of a compound according to claim 10.

20. A pharmaceutical composition comprising a compound according to claim 15 and a pharmaceutically acceptable carrier.

21. A method for treating cancer or inflammatory diseases in a subject in need thereof, comprising the administration of a therapeutically efficient amount of a compound according to claim 15.

22. A method for improving wound healing in a subject in need thereof, comprising the administration of a therapeutically efficient amount of a compound according to claim 15.

* * * * *